United States Patent
Imai et al.

(10) Patent No.: US 7,371,554 B2
(45) Date of Patent: May 13, 2008

(54) ISOZYMES OF LACRIMATOR COMPONENT SYNTHASE AND GENE ENCODING THE SAME

(75) Inventors: Shinsuke Imai, Osaka (JP); Nobuaki Tsuge, Osaka (JP); Muneaki Tomotake, Osaka (JP)

(73) Assignee: House Foods Corporation, Higashiosaka-shi (JP)

( * ) Notice: Subject to any disclaimer, the term of this patent is extended or adjusted under 35 U.S.C. 154(b) by 396 days.

(21) Appl. No.: 10/344,158

(22) PCT Filed: Aug. 30, 2001

(86) PCT No.: PCT/JP01/07465

§ 371 (c)(1),
(2), (4) Date: Feb. 10, 2003

(87) PCT Pub. No.: WO02/20808

PCT Pub. Date: Mar. 14, 2002

(65) Prior Publication Data

US 2005/0176126 A1    Aug. 11, 2005

(30) Foreign Application Priority Data

Sep. 4, 2000  (JP) ............................. 2000-267813

(51) Int. Cl.
  *C12N 9/00*   (2006.01)
  *C12N 9/88*   (2006.01)
  *C07H 21/04*   (2006.01)
(52) U.S. Cl. ...................... 435/232; 435/183; 536/23.2
(58) Field of Classification Search ................. 435/183; 530/23.2
  See application file for complete search history.

(56) References Cited

FOREIGN PATENT DOCUMENTS

JP  10-295373  11/1998

OTHER PUBLICATIONS

Van Damme et al. "Isolation and characterization of allinase cDNA clones from garlic (*Allium sativum L.*) and related species", Eur J Biochem. Oct. 15, 1992;209(2):751-7.*

Block E. et al., The organosulfer chemistry of the genus Allium: Implications for the oranic chemistry of sulfer. Angewandte Chemie International Edition in English, 1992, 31(9), pp. 1135-1178.

Krest I. et al., Cysteine sulfoxides and alliinase activity of some allium species. Journal of Agricultural and Food Chemistry, Aug. 2000, 48(8), pp. 3753-3760.

Kopsell D.E. et al., Changes in the S-alk(en)yl cysteine sulfoxides and their biosynthetic intermediates during onionstorage. Journal of the American Society for Horticultural Science, Mar. 1999, 124 (2), pp. 177-183.

Block, Eric. "The Organosulfur Chemistry of the Genus Allium—Implications for the Organic Chemistry of Sulfur", Angew. Chem. Int. Ed. Engl., vol. 31, No. 9, pp. 1135-1178 1992.

Krest, I. et al. "Cysteine Sulfoxides and Alliinase Activity of Some Allium Species", J. Agric. Food Chem, vol. 48, No. 8, pp. 3753-3760 2000.

Kopsell, David E. et al. "Changes in the S-alk(en)yl Cysteine Sulfoxides and their Biosynthetic Intermediates during Onion Storage", J. Amer. Soc. Hort. Sci., vol. 124, No. 2, pp. 177-183 1999.

* cited by examiner

*Primary Examiner*—Rebecca E. Prouty
*Assistant Examiner*—Iqbal Chowdhury
(74) *Attorney, Agent, or Firm*—Oblon, Spivak, McClelland, Maier & Neustadt, P.C.

(57) ABSTRACT

It is an object of the present invention to provide isozymes of the lachrymatory factor producing enzyme, the amino acid sequences of these isozymes and a gene that codes for these amino acid sequences, and the present invention relates to three types of isozymes of the lachrymatory factor producing enzyme that contributes to the production of the lachrymatory factor that is present in onions and the like, amino acid sequences indicated by SEQ ID Nos. 1 to 3 which constitute the proteins or polypeptides of these isozymes, DNA indicated by SEQ ID Nos. 4 and 5 which contains base sequences that code for the abovementioned proteins or polypeptides, a method of producing the abovementioned isozymes, a recombinant vector which contains the abovementioned DNA, a transformant formed by transforming a host cell with the abovementioned recombinant vector, a method of producing proteins or polypeptides that have lachrymatory factor producing enzyme activity by culturing the abovementioned host cell, and anti-sense RNA which has a base sequence that is complementary to that of the mRNA corresponding to the abovementioned DNA.

4 Claims, 9 Drawing Sheets

```
ACAATTCAGA CTCACATTAC GTTATATCAA GAAGATTGTC CAATCAGAAA AA ATG GAG CTA                    61
                                                            Met Glu Leu
                                                                -15
AAT CCT GGT GCA CCT GCT GTA GTC GCT GAT AGT GCT AAC GGA GCT CGA AAA TGG AGC GGC         121
Asn Pro Gly Ala Pro Ala Val Val Ala Asp Ser Ala Asn Gly Ala Arg Lys Trp Ser Gly
        -10             -5                   1                   5
AAA GTC CAT GCT TTG CTT CCA AAT ACA AAG CCA GAG CAA GCA TGG ACA CTA CTA AAA GAC         181
Lys Val His Ala Leu Leu Pro Asn Thr Lys Pro Glu Gln Ala Trp Thr Leu Leu Lys Asp
            10              15              20              25
TTT ATT AAC CTT CAC AAG GTC ATG CCT TCG TTG TCA GTC TGT GAA CTG GTA GAA GGT GAG         241
Phe Ile Asn Leu His Lys Val Met Pro Ser Leu Ser Val Cys Glu Leu Val Glu Gly Glu
            30              35              40              45
GCC AAT GTT GTT GGT TGT GTT CGC TAC GTT AAA GGT ATA ATG CAC CCA ATA GAA GAG GAA         301
Ala Asn Val Val Gly Cys Val Arg Tyr Val Lys Gly Ile Met His Pro Ile Glu Glu Glu
            50              55              60              65
TTT TGG GCC AAG GAG AAG CTG GTG GCG CTG GAT AAT AAG AAC ATG AGC TAC AGT TAT ATT         361
Phe Trp Ala Lys Glu Lys Leu Val Ala Leu Asp Asn Lys Asn Met Ser Tyr Ser Tyr Ile
            70              75              80              85
TTT ACT GAG TGT TTT ACA GGG TAC GAG GAT TAC ACG GCT ACC ATG CAA ATA GTG GAG GGT         421
Phe Thr Glu Cys Phe Thr Gly Tyr Glu Asp Tyr Thr Ala Thr Met Gln Ile Val Glu Gly
            90              95              100             105
CCT GAG CAC AAG GGA AGT AGA TTT GAC TGG TCT TTT CAG TGC AAG TAT ATC GAG GGT ATG         481
Pro Glu His Lys Gly Ser Arg Phe Asp Trp Ser Phe Gln Cys Lys Tyr Ile Glu Gly Met
            110             115             120             125
ACT GAA TCT GCA TTC ACC GAG ATT CTG CAG CAT TGG GCT ACT GAG ATA GGT CAG AAA ATC         541
Thr Glu Ser Ala Phe Thr Glu Ile Leu Gln His Trp Ala Thr Glu Ile Gly Gln Lys Ile
            130             135             140             145
GAA GAG GTT TGC AGT GCT TGATCATGAA TATCGGTTTT CAGTGCTGTG ATGCATTATG                     599
Glu Glu Val Cys Ser Ala
            150
TGTCTTTTAA ACCTTGTCTT GTGATATAAT AAAGTAACGT AATATGTGCA TGTAATAAGT                       659
AAGACTGAGT GTTGTGTGTT CAATAAAAAA GAATTTGCTT TTTGCAAGTT CTAGTGCTTT                       719
TCAAAAAAAA AAAAAAAA                                                                     737
```

Fig. 4

```
         10        20        30        40        50        60
AATTCGATTGATAGTGCGGACGGGGCGCGGAAATGGAGCGGCAAAGTCCATGCTTTGCTT
AsnSerIleAspSerAlaAspGlyAlaArgLysTrpSerGlyLysValHisAlaLeuLeu
         70        80        90       100       110       120
CCAAATACAAAGCCGGAGCAAGCATGGACACTACTAAAAGACTTTATTAACCTTCACAAG
ProAsnThrLysProGluGlnAlaTrpThrLeuLeuLysAspPheIleAsnLeuHisLys
        130       140       150       160       170       180
GTCATGCCTTCGTTGTCAGTCTGTGAACTGGTAGAAGGTGAGGCCAATGTTGTTGGTTGT
ValMetProSerLeuSerValCysGluLeuValGluGlyGluAlaAsnValValGlyCys
        190       200       210       220       230       240
GTTCGCTACGTTAAAGGTATAATGCACCCAATAGAAGAGGAATTTTGGGCCAAGGAGAAG
ValArgTyrValLysGlyIleMetHisProIleGluGluGluPheTrpAlaLysGluLys
        250       260       270       280       290       300
CTGGTGGCGCTGGATAATAAGAACATGAGCTACAGTTATATTTTTACTGAGTGTTTTACA
LeuValAlaLeuAspAsnLysAsnMetSerTyrSerTyrIlePheThrGluCysPheThr
        310       320       330       340       350       360
GGGTACGAGGATTACACGGCTACCATGCAAATAGTGGAGGGTCCTGAGCACAAGGGAAGT
GlyTyrGluAspTyrThrAlaThrMetGlnIleValGluGlyProGluHisLysGlySer
        370       380       390       400       410       420
AGATTTGACTGGTCTTTTCAGTGCAAGTATATCGAGGGTATGACTGAATCTGCATTCACC
ArgPheAspTrpSerPheGlnCysLysTyrIleGluGlyMetThrGluSerAlaPheThr
        430       440       450       460       470       480
GAGATTCTGCAGCATTGGGCTACTGAGATAGGTCAGAAAATCGAAGAGGTTTGCAGTGCT
GluIleLeuGlnHisTrpAlaThrGluIleGlyGlnLysIleGluGluValCysSerAla
        490       500       510       520       530       540
TGATCATGAATATCGTTTATGCTGTGATGCATTATTTGTGTTTTAAACCGTGTCCTGTGA
***
        550       560       570       580       590       600
TATAATAAAGTAACGTCATTTGTGCACGTAATAAGTAAAGCCCGAGTGTTGTGTGTTCAA 610       620       630       640       650       660
TAAAAAAGAACTTGCTTTTTGCAGGTTCTAGTGCTTTTCAAAAAAAAAAAAAAAAAAAAA

670
AAAAAATTCCTGC
```

Fig. 5

```
         10         20         30         40         50         60
AATTCGATTGATTCGGCGAATGGGGCGCGGAAGTGGAGCGGCAAAGTCCATGCTTTGCTT
AsnSerIleAspSerAlaAsnGlyAlaArgLysTrpSerGlyLysValHisAlaLeuLeu
         70         80         90        100        110        120
CCAAATACAAAGCCAGAGCAAGCATGGACACTACTAAAAGACTTTATTAACCTTCACAAG
ProAsnThrLysProGluGlnAlaTrpThrLeuLeuLysAspPheIleAsnLeuHisLys
        130        140        150        160        170        180
GTCATGCCTTCGTTGTCAGTCTGTGAACTGGTAGAAGGTGAGGCCAATGTTGTTGGTTGT
ValMetProSerLeuSerValCysGluLeuValGluGlyGluAlaAsnValValGlyCys
        190        200        210        220        230        240
GTTCGCTACGTTAAAGGTATAATGCACCCAATAGAAGAGGAATTTTGGGCCAAGGAGAAG
ValArgTyrValLysGlyIleMetHisProIleGluGluGluPheTrpAlaLysGluLys
        250        260        270        280        290        300
CTGGTGGCGCTGGATAATAAGAACATGAGCTACAGTTATATTTTTACTGAGTGTTTTACA
LeuValAlaLeuAspAsnLysAsnMetSerTyrSerTyrIlePheThrGluCysPheThr
        310        320        330        340        350        360
GGGTACGAGGATTACACGGCTACCATGCAAATAGTGGAGGGTCCTGAGCACAAGGGAAGT
GlyTyrGluAspTyrThrAlaThrMetGlnIleValGluGlyProGluHisLysGlySer
        370        380        390        400        410        420
AGATTTGACTGGTCTTTTCAGTGCAAGTATATCGAGGGTATGACTGAATCTGCATTCACC
ArgPheAspTrpSerPheGlnCysLysTyrIleGluGlyMetThrGluSerAlaPheThr
        430        440        450        460        470        480
GAGATTCTGCAGCATTGGGCTACTGAGATAGGTCAGAAAATCGAAGAGGTTTGCAGTGCT
GluIleLeuGlnHisTrpAlaThrGluIleGlyGlnLysIleGluGluValCysSerAla
        490        500        510        520        530        540
TGATCATGAATATCGGTTTTCAGTGCTGTGATGCATTATGTGTCTTTTAAACCTTGTCTT
***
        550        560        570        580        590        600
GTGATATAATAAAGTAACGTAATATGTGCATGTAATAAGTAAGACTGAGTGTTGTGTGTT 610        620        630        640        650        660
CAATAAAAAAGAATTTGCTTTTTGCAAGTTCTAGTGCTTTTCAAAAAAAAAAAAAAAAAA

670
AAAAAATTCCTGC
```

Fig. 6

ISOZYMES OF LACRIMATOR COMPONENT SYNTHASE AND GENE ENCODING THE SAME

TECHNICAL FIELD

The present invention relates to isozymes of a lachrymatory factor producing enzyme that contributes to the production of the lachrymatory factor that is generated when onions or the like are crushed or cut, and more particularly relates to three types of isozymes of a lachrymatory factor producing enzyme that has the activity of producing lachrymatory factor (thiopropanol S-oxide) from the enzyme aliinase decomposition products of the sulfur-containing compound PeCSO (S-1-propenyl-cysteine sulfoxide) that is present in onions and the like, the amino acid sequences of these isozymes, and DNA that codes for these isozymes or the like.

For example, the isozymes of the lachrymatory factor producing enzyme provided by the present invention, the amino acid sequences of these isozymes and the DNA that codes for these isozymes are useful as substances that can suppress the production of lachrymatory factor, as substances that can be used as selective markers for materials, materials for cross breeding or the like in the development of onion varieties in which the amount of lachrymatory factor that is generated in the case of disrupting or cutting is reduced, as substances that provide information for suppressing the amount of the abovementioned enzyme that is expressed, as substances for the mass production of the abovementioned enzyme, and as substances for the mass production of lachrymatory factor or the like.

BACKGROUND ART

Extensive research results concerning the lachrymatory factor that is generated when onions are crushed or cut have been reported in the past, and it is now believed that this lachrymatory factor is produced when S-1-propenyl-cysteine sulfoxide is degraded by aliinase.

However, according to research conducted by the present inventors, lachrymatory factor is not produced merely as a result of S-1-propenyl-cysteine sulfoxide being broken down by aliinase; the participation of other enzymes (lachrymatory factor producing enzymes) is indispensable.

Accordingly, as a result of diligent research, the present inventors developed a method of producing lachrymatory factor producing enzyme (an enzyme that produces a lachrymatory substance), and also clarified the physico-chemical properties of this lachrymatory factor producing enzyme; the inventors have previously field a patent application (Japanese Patent Application Laid-Open No. H10-295373) relating to this method.

Specifically, extensive research results regarding the formation and decomposition of the lachrymatory factor (LF) that is present in onions and the like have been reported in the past. However, in regard to the production mechanism of the abovementioned lachrymatory factor, it was believed in the past that the enzyme aliinase acts on the abovementioned precursor substance (PeCSO), and that a stable lachrymatory factor is formed non-enzymatically via sulfenic acid. On the other hand, research conducted by the present inventors has demonstrated that the abovementioned factor is actually not produced by the action of the enzyme aliinase alone, and that the participation of other enzymes is indispensable.

Accordingly, as a result of further diligent research, the present inventors discovered the existence of a new enzyme (lachrymatory factor producing enzyme) that apparently produces lachrymatory factor by isomerizing the abovementioned sulfenic acid. As a result, it was found that the abovementioned precursor substance is converted into lachrymatory factor (an aromatic component) or a different flavoring component depending on the action of the enzyme involved.

By using the amino acid sequence of this lachrymatory factor producing enzyme, and the DNA information that codes for this amino acid sequence, it is possible to achieve effect genetic recombination, mutation breeding, cross breeding and the like in the development of varieties of onions; this is useful for producing onions that tend not to generate lachrymatory factor even when crushed or cut.

Meanwhile, by utilizing DNA information that codes for the amino acid sequence of this lachrymatory factor producing enzyme, it is possible to produce this enzyme in large quantities by means of genetic recombination techniques and the like. For example, this is useful for the development of techniques for the efficient production of lachrymatory factor, which is useful in the treatment of alacrima (dry eye) and the like.

However, there have been absolutely no examples in the past of reports relating to the amino acid sequence of lachrymatory factor producing enzyme, or the DNA that codes for this amino acid sequence, so that no information has been available. As a result, research at the genetic level concerning lachrymatory factor producing enzyme has been difficult.

SUMMARY OF THE INVENTION

It is an object of the present invention to provide isozymes of lachrymatory factor producing enzyme, the amino acid sequences of the same, and a gene coding for the same or the like.

The present invention relates to three types of isozymes of the lachrymatory factor producing enzyme that contributes to the production of the lachrymatory factor that is present in onions and the like, the amino acid sequences indicated by SEQ ID Nos. 1 to 3, which are the proteins or polypeptides of these isozymes, the DNA indicated by SEQ ID Nos. 4 and 5, which contains base sequences that code for the abovementioned proteins or polypeptides, a method of producing the abovementioned isozymes, recombinant vectors which contain the abovementioned DNA, a transformant resulting from transformation performed by the abovementioned recombinant vectors, a method of producing proteins or polypeptides that have lachrymatory factor producing enzyme activity by culturing host cells of the abovementioned recombinant vectors, and anti-sense RNA which has a base sequence that is complementary to the mRNA corresponding to the abovementioned DNA.

DISCLOSURE OF THE INVENTION

Under such conditions, the present inventors conducted diligent research with the aim of explicating the lachrymatory factor producing enzyme that has the effect of producing lachrymatory factor from PeCSO present in onions and the like in the presence of the enzyme aliinase. As a result, the inventors succeeded in explicating a plurality of isozymes of the lachrymatory factor producing enzyme, the amino acid sequences of these isozymes, and the gene sequences that code for these amino acid sequences. This discovery led to the perfection of the present invention.

Specifically, it is an object of the present invention to provide three types of isozymes of the lachrymatory factor producing enzyme, and the amino acid sequences of these isozymes.

Furthermore, it is an object of the present invention to provide gene sequences that code for the isozyme proteins or polypeptides of the lachrymatory factor producing enzyme. Moreover, it is an object of the present invention to provide a method for controlling the action of the abovementioned isozymes of the lachrymatory factor producing enzyme, so that expression of the activity of the lachrymatory factor producing enzyme can be suppressed, and so that the production of onions in which this enzymatic activity is hindered can be realized.

In addition, it is an object of the present invention to provide recombinant vectors that have the abovementioned gene sequences, and to provide a method for realizing the efficient production of the isozymes of the lachrymatory factor producing enzyme by means of genetic recombination techniques.

The present invention which is used to solve the abovementioned problems comprises the following technical means:

(1) Isozymes of the lachrymatory factor producing enzyme which has the activity of producing lachrymatory factor by acting on lachrymatory factor precursors that are present in onions and the like, these isozymes being obtained by purifying the abovementioned lachrymatory factor producing enzyme utilizing differences in the isoelectric point of these isozymes.

(2) Proteins or polypeptides which contain the amino acid sequence indicated by SEQ ID No. 1, or amino acid sequences in which one or more amino acids in this amino acid sequence are added, deleted or replaced, and which have lachrymatory factor producing enzyme activity.

(3) Proteins or polypeptides which contain the amino acid sequence indicated by SEQ ID No. 2, or amino acid sequences in which one or more amino acids in this amino acid sequence are added, deleted or replaced, and which have lachrymatory factor producing enzyme activity.

(4) Proteins or polypeptides which contain the amino acid sequence indicated by SEQ ID No. 3, or amino acid sequences in which one or more amino acids in this amino acid sequence are added, deleted or replaced, and which have lachrymatory factor producing enzyme activity.

(5) DNA containing a base sequence which codes for the proteins or polypeptides described in (2), (3) or (4) above.

(6) The DNA described in (5) above, in which the base sequence that codes for proteins or polypeptides is DNA indicated by SEQ ID No. 4.

(7) The DNA described in (5) above, in which the DNA containing the base sequence that codes for proteins or polypeptides is DNA indicated by SEQ ID No. 5.

(8) A method of producing isozymes of the lachrymatory factor producing enzyme, which is characterized in that the lachrymatory factor producing enzyme that produces lachrymatory factor by acting on lachrymatory factor precursors that are present in onions and the like is purified from the enzyme-by utilizing differences in the isoelectric point of these isozymes, to isolate the isozyme E2-1, E2-2 or E2-3.

(9) A method of producing proteins or polypeptides that have lachrymatory factor producing enzyme activity, which is characterized in that a protein or polypeptide with lachrymatory factor producing enzyme activity is isolated, that is produced in a culture medium or cells by culturing host cells transformed by a recombinant vector containing the DNA described in (5), (6) or (7) above.

(10) Anti-sense RNA which is characterized in that this RNA has a base sequence being complementary to that of the mRNA corresponding to the DNA described in (5),(6) or (7) above.

Next, the present invention will be described in greater detail.

In the present invention, in order to achieve the abovementioned objects, the isozymes contained in a lachrymatory factor producing enzyme (E2) mixture purified by ordinary methods are first separated by an isoelectric point electrophoresis or chromato-focusing method utilizing differences in the isoelectric point of the enzyme, so that three types of isozymes are isolated. Next, the N terminal amino acid sequences are clarified for the three types of isolated isozymes, these primers are designed on the basis of the gene base sequence predicted from these amino acid sequences, and a gene for the lachrymatory factor producing enzyme is selectively synthesized by the PCR method using cDNA prepared from the mRNA of an onion as a template. As a result of analyzing the structure of the gene thus obtained, the present inventors confirmed that one open reading frame was detected, and that since the molecular weight of the mature protein predicted from this agreed with the measured values (MALDI-TOFMS) of the molecular weights of the isolated isozymes, the abovementioned gene is the gene for lachrymatory factor producing enzyme.

The lachrymatory factor producing enzyme that produces lachrymatory factor (thiopropanol S-oxide) from the decomposition products of S-1-propenyl-cysteine oxide (PeCSO) produced by aliinase is an important component for modifying the flavor and improving the processing characteristics of onions. Accordingly, determination of the amino acid sequence of this lachrymatory factor producing enzyme and the gene sequence that codes for this amino acid sequence is extremely significant in the fields of plant breeding and production of lachrymatory factor producing enzyme.

The present inventors initiated research with the aim of clarifying the amino acid sequence of the abovementioned lachrymatory factor producing enzyme (E2) and the gene sequence that codes for this amino acid sequence. Specifically, if the genetic information of the abovementioned lachrymatory factor producing enzyme can be explicated, then application of this information to for example the development of onion varieties in which lachrymatory factor is not produced during the processing of the onions may be expected. Accordingly, research was begun with the aim of determining the structural gene sequence of E2, and clarifying the gene and amino acid sequences of the same.

However, as this research was pursued, it was found that determination of the N terminal amino acid sequence is difficult in the case of purified enzyme samples of E2 obtained using ordinary purification methods. Specifically, an investigation by the present inventors demonstrated that a plurality of isozymes are contained in the E2 obtained by a conventional method developed by the present inventors, and that it is therefore necessary to isolate these isozymes before the amino acid sequence of E2 and the base sequence that codes for this amino acid sequence can be explicated. On the basis of these findings, the present inventors conducted further research, and subsequently isolated three main types of isozymes (E2-1, E2-2 and E2-3) of E2, and determined the N terminal amino acid sequences of these isozymes. The inventors designed these primers on the basis of these findings, and succeeded in determining the gene sequences that code for the respective E2 isozymes, and the amino acid sequences of these isozymes, using methods such as PCR and the like.

Furthermore, to describe this point in detail, lachrymatory factor producing enzyme samples purified by conventional methods were detected as one band in SDS-PAGE electrophoresis; accordingly, it was inferred that the enzyme consisted of a single protein, and an N terminal amino acid analysis was attempted. However, since a plurality of isozymes were present as a mixture in these partially purified samples, the N terminal amino acid sequence could not be specified.

Accordingly, various investigations were made concerning types of ion exchange resins and elution conditions, and also concerning the size of the gel filtration column and the type of gel used, and an attempt was made to isolate the isozymes. However, such isolation could not be accomplished regardless of the method used. On the other hand, in the case of electrophoresis using a native polyacrylamide gel, the isozymes were successfully detected as a plurality of bands. Accordingly, a method was tried in which purification was accomplished by cutting the isozymes from the gel. In the case of this method, however, the isolation of the respective isozymes was insufficient, and the positions of the isozymes that were cut out fluctuated with each electrophoresis operation; as a result, accurate cutting could not be achieved, so that high-purity isozymes could not be obtained. As a result of repeating these trials, it was found that that the plurality of isozymes could be efficiently isolated by using isoelectric point gel electrophoresis or chromato-focusing, which are methods that utilize differences in the isoelectric point.

Furthermore, in the case of isoelectric point electrophoresis, a method can be used in which for example electrophoresis is performed using a polyacrylamide gel containing ampholine with a pH of 4.0 to 6.5, the gel is cut out following electrophoresis, and the isozymes are isolated by elution using water or a buffer. In the case of chromato-focusing, for example, a Mono P column (manufactured by Pharmacia) can be equilibrated with an anhydrous piperazine-HCl buffer, and the isozymes can then be isolated by elution with a buffer using Poly Buffer 74 (manufactured by Pharmacia).

The principal isozymes contained in the partially purified samples were of three types (E2-1, E2-2, E2-3). These three types of isozymes were purified using isoelectric point gel electrophoresis or chromato-focusing. However, even when such purification methods were used, it was necessary to repeat the purification operation several times in order to obtain high-purity isozymes. Using such a process, the present inventors succeeded in isolating the three main types of isozymes.

The abovementioned lachrymatory factor producing enzyme samples are ideally prepared by extraction and purification using onions or the like as a raw material. However, materials other than onions can also be used as raw materials as long as these materials contain the abovementioned enzyme in the same manner as onions. In this case, for example, the following methods may be cited as ideal methods for the abovementioned extraction and purification processes.

For example, onions are used as a raw material, and this material is mixed with water and crushed using a mixer or the like. The crushed matter thus obtained is centrifuged, and the supernatant liquid is salted out so that the protein is precipitated. Next, the abovementioned precipitate is dissolved in a buffer solution such as a phosphate buffer or the like; then, this solution is centrifuged, and the supernatant liquid is collected as a crude enzyme solution.

Here, various types of buffers may be used; examples include potassium phosphate buffers, citrate buffers, acetate buffers, tartarate buffers, succinate buffers, maleate buffers, tris-HCl buffers, citrate-phosphate buffers and the like.

Next, a partially produced enzyme solution can be obtained by subjecting the crude enzyme solution obtained by the abovementioned method to a purification treatment using an appropriate combination of means such as hydroxyapatite, ammonium sulfate precipitation, dialysis, anion exchange and gel filtration or the like.

The partial purification of the abovementioned enzyme from the crude enzyme solution is not limited to the method described above; universally known separation and purification methods can be used. For example, the crude enzyme protein can be obtained from the crude enzyme solution by ammonium sulfate precipitation, precipitation using an organic solvent or the like; furthermore, this crude protein can be subjected to a purification treatment by using an appropriate combination of ion exchange, gel filtration and various types of chromatography such as affinity chromatography or the like.

Examples of concrete methods that can be used to acquire the cDNA of the isozymes of the abovementioned lachrymatory factor producing enzyme include a method in which a cDNA probe is prepared on the basis of the respective N terminal amino acid sequences of E2-1 through E2-3, and the cDNA of E2 is pulled up by hybridization from a cDNA library prepared using the mRNA of E2 extracted from onion bulbs as a template, and a method in which an anchor is added to the poly A chain of the mRNA, the 3' terminal side sequence of E2 is clarified by the PCR method using a primer which is complementary to this chain and a primer that is prepared on the basis of the respective N terminal amino acid sequences of E2-1 through E2-3, and using cDNA synthesized from the mRNA as a template, and the 5' terminal side sequence is then clarified using the 5' RACE method. Ideally, the gene sequences of the abovementioned three types of isozymes can be determined for example by the method described below. However, the present invention is not limited to the following method.

1) Total RNA is extracted from bulbs of onions by the phenol/SDS/LiCl method.

2) The total RNA is treated with an oligo-dT column so that the mRNA is purified.

3) cDNA is synthesized by treating the mRNA with a reverse transcription enzyme.

4) PCR is performed using a degenerate primer and a primer corresponding to the anchor part attached to the poly A chain terminal, prepared on the basis of five residues of the N terminal amino acids of E2-1, so that an amplification product originating on the downstream side of E2-1 obtained.

5) The PCR amplification product thus obtained is purified, after which the base sequence is clarified by sub-cloning.

6) The fact that the amplification product obtained by PCR originates in E2-1 is confirmed by the fact that the results of the measurement of the molecular weight of E2-1 by MALDI-TOFMS shows good agreement with the molecular weight predicted from the amino acid sequence.

7) PCR (5' RACE) is performed using a primer designed from the internal sequence of E2-1 and a primer designed from the anchor attached to the oligo-dC chain that is added to the 5' terminal, so that an amplification product originating on the upstream side is obtained.

8) The PCR amplification product thus obtained is purified, after which the base sequence is clarified by sub-cloning.

The presence of an open reading frame (ORF) of E2-1 was confirmed by analyzing the sequence analysis results. As a result, it was demonstrated that after E2-1 is synthesized as a protein consisting of 169 amino acids, 16 amino acids of the N terminal are removed by processing, thus producing a mature protein.

Specifically, as a result of acquiring and analyzing the cDNA of the isozymes of the abovementioned lachrymatory factor producing enzyme, it was found that the abovementioned E2-1, E2-2 and E2-3 are translated into proteins on the basis of the same gene, and that E2-1, E2-2 and E2-3 are formed as a result of differences in subsequent processing. Furthermore, it was also found that in the case of the second amino acid from the N terminal of E2-2 and the fourth amino acid from the N terminal of E2-3, Asn changes to Asp following translation. In this way, the gene sequences and primary sequences of the amino acids of E2-1, E2-2 and E2-3 were determined.

It became clear from the experimental results that E2-2 and E2-3 are isozymes that are synthesized on the basis of the same gene, and that are produced by differences in processing.

As a result of the analysis of the N terminal amino acid sequence of E2-3 to 10 residues, it was found that the five residues of the N terminal amino acid sequence of E2-2 show complete agreement with the third through seventh residues of the N terminal of E2-3.

```
(N Terminal Amino Acid Sequence of E2-2)
(amino acids 1 to 5 of SEQ ID NO:2)
Ala Asp Gly Ala Arg (N Terminal Amino Acid Sequence of E2-3)
(amino acids 1 to 10 of SEQ ID NO:3)
Asp Ser Ala Asp Gly Ala Arg Lys Trp Ser
```

It was found from these results that E2-3 is a protein in which Ser and Asp are added to the N terminal side of E2-2.

It appears from the above results that E2-2 and E2-3 are synthesized on the basis of the same gene.

Next, in order to elucidate the gene sequence of E2-3, PCR is performed using a degenerate primer prepared on the basis of nine residues of the N terminal amino acids of E2-3, and a primer designed from the anchor attached to the poly A chain terminal, so that an amplification product is obtained.

After the PCR amplification product thus obtained is purified, the base sequence is clarified by sub-cloning.

As a result of analyzing the sequence analysis results, it was found that the sequence on the downstream side of E2-3 agrees with the sequence confirmed in E2-1.

Here, since the sequence on the downstream side of E2-3 agrees with the sequence confirmed in E2-1, the primer used for 5' RACE is the same as the primer used to confirm the upstream sequence of E2-1.

Since a common anchor primer is used in the case of 5' RACE, assuming that the upstream sequence of E2-3 differs from the upstream sequence of E2-1, it appears that both the upstream sequence of E2-3 and the upstream sequence of E2-1 may be contained in the amplification product of 5' RACE performed using E2-1.

Accordingly, DNA was extracted from different recombinant colonies, and the 5' RACE product of E2-1 was further sequenced twice.

As a result of analysis, it was found that the sequences of the two additional 5' RACE products agreed with the upstream sequence of the previously analyzed E2-1.

As a result of the above, it appears highly probable that the upstream sequence of E2-3 is also the same as the upstream sequence of E2-1.

Accordingly, as a result of various investigations, it was concluded that E2-3 is translated on the basis of the same gene as E2-1, and that there is a change from Asn to Asp in the process by which the mature protein is formed.

That the above conclusion is correct can also be confirmed from the fact that the molecular weight measurement results obtained for E2-2 and E2-3 by MALDI-TOFMS show good agreement with the molecular weights predicted from the amino acid sequences.

The molecular weight of E2-2 (155 amino acids) is 17689, and the measured value is 17722.

The molecular weight of E2-3 (157 amino acids) is 17892, and the measured value is 17909.

Next, the optimal pH and optimal temperature in the mixed system of PeCSO, aliinase and E2 will be described.

The optimal pH for E2 is 4.5 to 5.0 in all cases, with no great difference being seen in the three isozymes.

In regard to the optimal temperature for E2-1 through E2-3 as well, it as found that this temperature is in the temperature range of 15° C. to 25° C., with no great difference being seen.

The abovementioned three isozymes all show conspicuous agreement in terms of molecular weight, optimal pH and action of producing lachrymatory factor. In the present invention, all of the isozymes are included in the isozymes of the abovementioned lachrymatory factor producing enzyme provided by the present invention.

Furthermore, when the N terminal amino acids were analyzed using E2-1 as a sample, two other types of isozymes (named E2-1-1 and E2-1-2) were detected in small amounts, and the N terminal amino acid sequences of these isozymes were also determined.

Specifically, in addition to the abovementioned three types of isozymes, minor isozymes (E2-1-1 and E2-1-2) were also present in crudely purified E2 samples.

The N terminal amino acid sequences and molecular weight measurement values for the respective isozymes are shown below.

| (Isozyme) | (N Terminal Amino Acid Sequence) | | Molecular Weight (MALDI-TOFMS) |
|---|---|---|---|
| E2-1 | Gly Ala Arg Lys Trp | (amino acids 1 to 5 of SEQ ID NO:1) | 17465 |
| E2-1-1 | Ala Arg Lys Trp | (amino acids 2 to 5 of SEQ ID NO:1) | |
| E2-1-2 | Ser Ala Asn Gly Ala | (amino acids 2 to 6 of SEQ ID NO:3) | |

-continued

| (Isozyme) | (N Terminal Amino Acid Sequence) | | Molecular Weight (MALDI-TOFMS) |
|---|---|---|---|
| E2-2 | Ala Asp Gly Ala Arg | (amino acids 1 to 5 of SEQ ID NO:2) | 17722 |
| E2-3 | Asp Ser Ala Asp Gly Ala Arg Lys Trp Ser | (amino acids 1 to 10 of SEQ ID NO:3) | |

It appears that the second Asp from the N terminal of E2-2 and the fourth Asp from the N terminal of E2-3 are converted into Asp after being synthesized in the form of Asn; accordingly, it is inferred that E2-2 and E2-3 in which the Asp in the abovementioned positions is Asn also exist. The molecular weights ascertained from the sequences were 17503 in the case of E2-1 (153 amino acids), 17689 in the case of E2-2 (155 amino acids) and 17892 in the case of E2-3 (157 amino acids); these values are close to the measured values obtained by MS.

The DNA that codes for the isozymes of the lachrymatory factor producing enzyme provided by the present invention includes DNA expressed by the base sequence indicated by SEQ ID No. 4, and DNA that codes for proteins or polypeptides including derivatives obtained by adding, deleting or replacing one or more amino acids in the abovementioned protein amino acid sequence.

The proteins or polypeptides of the present invention that have lachrymatory factor producing enzyme activity include proteins or polypeptides which have the abovementioned enzymatic activity, including derivatives obtained by adding, deleting or replacing amino acids in the abovementioned protein amino acid sequence, and proteins or polypeptides which are expressed by the amino acid sequences indicated by SEQ ID Nos. 1 to 3, and which have the abovementioned enzymatic activity.

The DNA that codes for the abovementioned E2 isozyme of the present invention, and the abovementioned amino acid sequences, are useful as markers for realizing methods of selecting onions for cross breeding, methods for creating onion varieties in which lachrymatory factor producing enzyme activity is reduced, and methods for producing the lachrymatory factor producing enzyme in large quantities by means of genetic recombination techniques or the like.

The following may be cited as examples of application of the isozymes of the lachrymatory factor producing enzyme provided by the present invention:

(1) Production of Lachrymatory Factor Producing Enzyme

Recombinant vectors can be prepared by incorporating the cDNA of the isozymes of the lachrymatory factor producing enzyme obtained as described above into appropriate expression vectors.

The vectors used can be copied autonomously inside host cells; there are no particular restrictions on the types of vectors used as long as these vectors have a cloning site that allows the incorporation of the abovementioned DNA, i. e., the E2 isozyme gene, and have a region that makes it possible to express the incorporated DNA inside the host cells.

Furthermore, DNA which has been designed and synthesized to code for the proteins or polypeptides of the present invention that have lachrymatory factor producing enzyme activity can be used as the E2 isozyme gene that is incorporated into a vector. Moreover, in order to promote expression in host cells into which the DNA is incorporated, codons may be transformed in accordance with the type of host into which the DNA is incorporated; it goes without saying that such codon-transformed DNA is also included in the scope of the present invention. The synthesis of genes on the basis of such amino acid sequences may be appropriately accomplished by methods such as the connection of oligonucleotides synthesized using the auto-synthesis function of DNA following annealing or the like.

Furthermore, in the case of E2-1, E2-2 and E2-3, there is a possibility that the same enzymatic nature as that of natural E2 will be obtained even if one or more amino acids are added or deleted, as is also evident from the fact that the enzymatic natures of these isozymes show conspicuous agreement in spite of the fact that the N terminal amino acid sequences are different. Furthermore, even if some of the amino acid residues are replaced, there is a possibility that the same enzymatic nature as that of natural E2 will be obtained. Such genetic modifications can easily be realized using a commercially marketed gene position-specific mutation introduction kit, or by using a method such as the insertion of synthetic genes or the like. Accordingly, as long as the same enzymatic nature as that of natural E2 is maintained, a mutant form may be used as the E2 isozyme gene that is incorporated into a vector. Next, the abovementioned recombinant expression vector is introduced into a host cell, so that a transformation product is obtained. The introduction of the recombinant expression vector into the host cell can be accomplished by customary methods. Examples of methods that can be used include various methods such as the competent cell method, protoplast method, calcium phosphate co-precipitation method, electro-poration method, micro-injection method, liposome fusion method and the like. Any desired method may be used in accordance with the host that is used. Ideal examples of hosts that produce the E2 isozymes of the present invention include microorganisms such as *Escherichia coli* bacteria, *Bacillus*, yeasts or *Aspergillus*, or cells such as silkworm-cultured cells or the like.

Isozymes of E2 can be produced in a culture by culturing the transformant obtained as described above. Isozymes of the abovementioned lachrymatory factor producing enzyme can be stably obtained from such a culture by isolation or purification using universally known methods.

(2) Production of Plants That Do Not Produce Lachrymatory Factor by Means of Anti-Sense RNA The expression of the abovementioned genetic information can be suppressed by expressing anti-sense RNA inside plants on the basis of the base sequence of the gene that codes for the isozymes of E2 provided by the present invention. This anti-sense RNA has a base sequence that is complementary to that of the mRNA, and forms base pairs with the mRNA so that the genetic information is blocked, thus inhibiting the synthesis of the proteins of the isozymes of E2 that constitute the final products. The anti-sense RNA that can be used in the present invention consists of oligonucleotides obtained by specific hybridization with mRNA synthesized on the basis of the base sequence indicated by SEQ ID No. 5.

The target sites of anti-sense nucleotides vary according to the gene involved, and there is no consensus as to which position is invariably the best. Generally, however, ATG starting sites or the like may be candidates for target sites. Recently, furthermore, several types of computer analysis software for designing target sites and anti-sense nucleotides (HYB Simulator and the like) have appeared on the market; accordingly, it is also possible to design anti-sense nucleotides utilizing such software. Moreover, it is desirable that the length of such anti-sense nucleotides be 18 to 23 mer, and that the GC content be 50% or greater.

For instance, a method in which RNA is synthesized by incorporating cDNA in a reverse orientation on the downstream side of the promoter of the expression vector and introducing this into a host cell may be cited as an example of a method for causing the abovementioned anti-sense RNA to function inside a plant.

A transformation method using Agrobacterium or a transformation method using direct introduction may be used as methods for introducing foreign genes; however, in the case of monocotyledonous plants such as onions and the like, especially good results are obtained by a transformation method using direct introduction (see Klein, T. M. et al., Nature 327, 70-73, 1987); accordingly, a method using direct introduction is desirable.

(3) Mass Production of E2 Proteins

For example, expression vectors containing DNA which has base sequences that code for polypeptides of the E2 proteins in the present invention can be manufactured by (a) isolating RNA that codes for E2, (b) synthesizing single-stranded cDNA, and then double-stranded DNA, from this RNA, (c) introducing this cDNA into a plasmid, (d) transforming a host using the plasmid thus obtained, (e) culturing the transformant thus obtained, and then isolating the desired plasmid by an appropriate method, (f) cutting out the cloned DNA from this plasmid, and (g) connecting this cloned DNA to the downstream side of the promoter of the expression vector.

The RNA that codes for E2 may be RNA from materials other than onions, as long as these materials contain E2. Examples of methods that can be used to prepare RNA from materials containing E2 include the phenol/SDS method, LiCl method (Saibo Kogaku Bessatsu [Cell Engineering Special Edition], Saibo Kogaku Shiriizu [Cell Engineering Series] 2, Shokubutsu no PCR Jikken Control [PCR Experimental Control in Plants], p. 51, Shujunsha) and the like. With the RNA thus obtained used as a template, cDNA can be synthesized using a reverse transcription enzyme, and the cDNA thus obtained can be incorporated into a plasmid.

Examples of plasmids into which such cDNA can be incorporated include pBR322 (Gene, 2, 95 (1977)) and pBR325 (Gene, 4, 121 (1978) originating in coliform bacteria, pUB110 originating in Bacillus (Biochemical and Biophysical Research Communication, 112, 678 (1983) and the like; however, any other type of plasmid may also be used as long as this plasmid can be copied and retained inside the host. In regard to the method used for incorporation into the plasmid, a method in which a mixed solution in which the molar ratio of the vector and insert is adjusted to a value in the range of 1:1 to 1:10 and this mixed solution is treated with T4 ligase is generally used (Saibo Kogaku Bessatsu [Cell Engineering Special Edition], Baio-Jikken Irasutoreiteddo [Bio-Experiments Illustrated], (2) Idenshi Kaiseki Kiso [Fundamentals of Genetic Analysis], p. 78, Shujunsha). The plasmid obtained in this manner is introduced into an appropriate host, e. g., an organism of the genus *Escherichia*, and organism of the genus *Bacillus*, or the like.

Examples of the abovementioned organisms of the genus *Escherichia* include *Escherichia coli* (Proc. Natl. Acad. Sci. U.S.A., 60, 160, 1968) and the like. Examples of the abovementioned organisms of the genus *Bacillus* include *Bacillus* subtilis MI114 (Gene, 24, 255 (1983)) and the like. The calcium chloride method (Biochemical and Biophysical Research Communication, 49, 1568 (1972)) and the like may be cited as examples of methods that can be used for transformation. From the transformant thus obtained, the desired clone can be selected using universally known methods, e. g., the colony hybridization method (Gene, 10, 63 (1980) and the DNA base sequence determination method (Proceedings of the National Academy of Sciences, 74, 560 (1977)) or the like. In this way, a microorganism which holds a vector that has DNA containing the base sequence that codes for the cloned E2 is obtained.

Next, the plasmid is isolated from the microorganism. The alkali method (Nucleic Acids Research, 1513 (1979)) and the like may be cited as examples of isolation methods that can be used. The plasmid containing the base sequence that codes for the abovementioned cloned E2 may be used "as is", or if desired, may be cut out by means of a restriction enzyme. An expression vector can be obtained by connecting the cloned gene to the downstream side of the promoter in a vector that is suitable for expression.

Examples of vectors that can be used include plasmids originating in *Escherichia coli* bacteria (e. g., pBR322), plasmids originating in *Bacillus* (e. g., pUB110), plasmids originating in yeasts (e. g., pSH19), and bacteriophages such as λ phage or the like, as well as animal-viruses such as retroviruses, vaccinia virus or the like. The abovementioned gene may have ATG as a translation-initiating codon on the 5' terminal of the gene, and may have TAA, TGA or TAG as a translation-terminating codon on the 3' terminal. Furthermore, in cases where the 5' terminal of the abovementioned gene is bound to the 3' terminal of a gene that codes for a known protein so that the gene is expressed as a fused protein, a translation-initiating codon is not absolutely necessary. Furthermore, a promoter is connected to the upstream side of the abovementioned gene in order to express the gene. The promoter used in the present invention may be any promoter that is appropriate for the expression of the gene in accordance with the host that is used. Furthermore, in cases where the host used for transformation is an organism of the genus *Escherichia*, a trp promoter, lac promoter, recA promoter or the like is desirable. In cases where the host is an organism of the genus *Bacillus*, an SPO1 promoter, SPO2 promoter, penP promoter or the like is desirable. In cases where the host is a yeast, a PHO5 promoter, PGK promoter, GAP promoter or the like is desirable. Especially in cases where the host is an organism of the genus *Escherichia*, it is desirable that the promoter used be an lac promoter. In case where the host is an animal cell, a promoter originating in SV40, a retrovirus promoter or the like may be used. In this case, a promoter originating in SV40 is especially desirable.

A transformant product is prepared using a vector containing DNA constructed in this manner. Examples of hosts that can be used include organisms of the genus *Escherichia*, organisms of the genus *Bacillus*, yeasts, animal cells and the like. The same examples as those mentioned above may be cited as concrete examples of the abovementioned organisms of the genus *Escherichia* and organisms of the genus *Bacillus*. *Saccharomyces cerevisiae* AH22R and the like may be cited as examples of the abovementioned yeasts. Passing cells COS-7, Vero, Chinese hamster cells CHO and the like may be cited as examples of animal cells. In this way, a transformant that has been transformed by the vector containing the abovementioned DNA is obtained.

The *Escherichia coli* BL21/pGEX-4T-3-E2-3-1 obtained in Example (11) described later may be cited as one example. This microorganism was deposited with the deposit number of FERM BP-7675 in International Patent Organism Depositary, National Institute of Advanced Industrial Science and Technology on Jul. 25, 2001 in accordance with the Budapest treaty, and is stored at the same laboratory. When a transformation product in which the host is an organism of the genus *Escherichia* or an organism of the genus *Bacillus* is cultured, a liquid culture medium is appropriate as the culture medium that is used for culturing. The carbon source, nitrogen source, inorganic substances and the like that are necessary for the growth of the transformant are included in this culture medium.

For example, an LB culture medium or SOC culture medium (Saibo Kogaku Bessatsu [Cell Engineering Special Edition], Baio Irasutoreiteddo [Bio Illustrated], 1. Bunshiseibutsugaku Jikken no Kiso [Fundamentals of Molecular-Biological Experiments], p. 98-99, Tojunsha) is desirable. Here, if necessary, an agent such as isopropyl-1-thio-β-D-galactoside (IPTG) may be added in order to cause efficient movement of the promoter. In cases where the host is an organism of the genus *Escherichia*, culturing is ordinarily performed for 3 to 24 hours at 15 to 43° C.; if necessary, ventilation and agitation may also be applied. In cases where the host is an organism of the genus *Bacillus*, culturing is ordinarily performed for approximately 6 to 24 hours at a temperature of approximately 30 to 40° C.; if necessary, ventilation and agitation may also be applied. In cases where the host is an organism of the yeast is cultured, for example, a Burkholder minimal culture medium (Proceedings of the National Academy of Sciences 77, 4505 (1980) or the like may be used as the culture medium. It is desirable that the pH of the culture medium be adjusted-to approximately 5 to 8. Culturing is ordinarily performed for approximately 24 to 72 hours at a temperature of 20° C. to 35° C.; if necessary, ventilation and agitation may be applied. In cases where the host is an organism of the animal cell is cultured, a MEN culture medium (Science 122, 501 (1952)) or DMEM culture medium (Virology, 8, 396 (1959)) containing approximately 5to 20% bovine fetal serum may be cited as examples of culture media that can be used. It is desirable that the pH be approximately 6 to 8. Culturing is ordinarily performed for approximately 15 hours to 60 hours at a temperature of approximately 30° C. to 40° C.; if necessary, the carbon dioxide concentration can be increased.

For example, the method described below can be used in order to separate E2 proteins from the abovementioned cultures and purify these proteins. In order to separate E2 proteins from the culture mass or cells, a method in which the organism mass or cells are collected by universally known methods following culturing, and are suspended in a buffer solution containing a protein-modifying agent such as guanidine hydrochloride or the like, after which the organism mass or cells are disrupted by ultrasonic vibration, lisozyme and/or freezing and melting, and E2 proteins are then obtained by centrifugal separation, can be appropriately used. The purification of E2 proteins from the abovementioned supernatant liquid can be accomplished by appropriately combining separation and purification methods that are in themselves universally known. Examples of such universally known separation and purification methods include methods that utilize solubility such as salting-out methods, solvent precipitation methods and the like, methods that utilize differences in molecular weight such as dialysis methods, gel filtration methods and the like, methods that utilize differences in charge such as ion exchange chromatography and the like, methods that utilize specific affinities such as affinity chromatography and the like, and methods that utilize differences in hydrophobicity such as reverse-phase high-speed liquid chromatography and the like.

BRIEF DESCRIPTION OF THE DRAWINGS

FIG. 4 shows the full-length base sequence consisting of 737 bases, and the amino acid sequence of E2;
FIG. 5 shows the bases of E2-3-1 consisting of 673 bases, and the amino acid sequence consisting of 160 amino acids, cut out using EcoRI and NotI;
FIG. 6 shows the bases of E2-3-2 consisting of 673 bases, and the amino acid sequence consisting of 160 amino acids, cut out using EcoRI and NotI.

BEST MODE FOR CARRYING OUT THE INVENTION

Next, the present invention will be concretely described in terms of examples; however, the present invention is not limited in any way by the following examples.

EXAMPLES (1) Isolation of Isozymes of Lachrymatory Factor Producing Enzyme

The lachrymatory factor producing enzyme samples were prepared by a conventional method developed by the present inventors (Japanese Patent Application Laid-Open No. 10-295373), using onions as a raw material.

1) Purification by Chromato-Focusing

A Mono P HR5/20 column (5ϕ×200 mm) (manufactured by Pharmacia), which is a chromato-focusing column, was equilibrated with a start buffer (0.025 M anhydrous piperazine adjusted to a pH of 5.7 with HCl), after which 500 μl of sample was applied. Following this application, the sample was eluted with an eluent buffer (10% Poly buffer (manufactured by Pharmacia) adjusted to a pH of 4.0 with HCl), and the eluate was fractionated and recovered. The flow rate of the eluate was set at 0.5 ml/min, and the temperature was set at 4° C.; the absorption at 280 nm and the lachrymatory factor producing enzyme activity were measured.

2) Method Used to Measure Activity

The method used to measure the activity was as follows: specifically, the sample was diluted with a diluent buffer (50 mM potassium phosphate buffer, pH 6.5); then, 40 µl of garlic aliinase (50 units/ml) and 20 µl of a solution of PeCSO (20 mg/ml) were added to 10 µl of the diluted sample, and a reaction was performed for 3 minutes at room temperature. Afterward, 1 µl of the reaction solution was applied to HPLC, and the amount of lachrymatory factor produced was determined. Furthermore, an OSD column (4.6φ×250 mm) (manufactured by Senshu Kagaku Co.) or a DOCOSIL column (4.6φ×250 mm) (manufactured by Senshu Kagaku Co.) was used for analysis. In addition, 30% (v/v) acidic MeOH was used for the mobile phase, the flow rate was set at 0.6 ml/min, the column temperature was set at 35° C., and detection was performed at 254 nm.

3) Results

As a result of purification using a Mono P column, it was found that a plurality of isozymes are present in E2, and that three types of these isozymes are present in high concentrations. Accordingly, these three types of isozymes (E2-1, E2-2, E2-3) were isolated.

Figure 1:
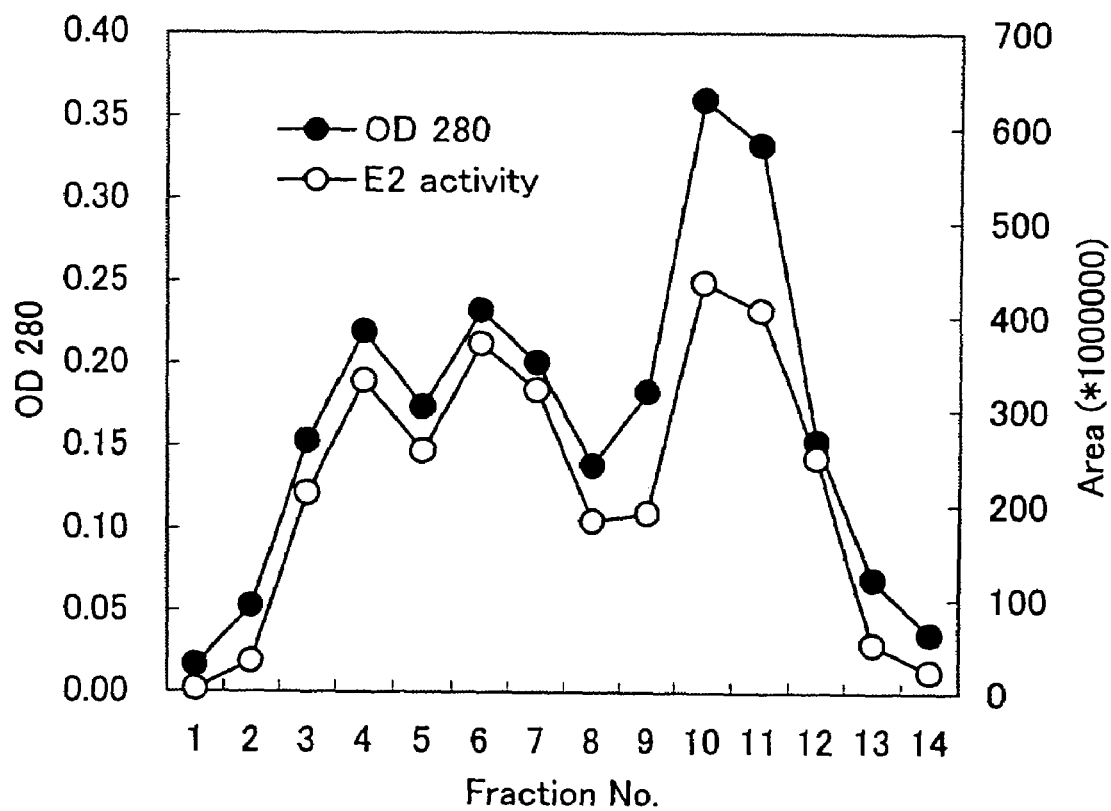
FIG. 1 shows the elution pattern in the case of Mono P.

FIG. 1 shows a typical pattern of elution from the Mono P column. Here, E2-1 is fraction No. 4, E2-2 is fraction No. 6, and E2-3 consists of fractions No. 10 and 11. Furthermore, E2-1-1 and E2-1-2 were contained as trace components in E2-1.

The isozymes of E2 for which the N terminal amino acid sequences could be confirmed consisted of a total of five types of isozymes, i. e., three types with large contents and two types with small contents.

(2) Comparison of Optimal pH Values and Optimal Temperatures of Isozymes

Respective samples of purified E2-1, E2-2 and E2-3 were diluted with a 350 mM potassium phosphate buffer (pH 2.4 to 8.0), and the activity measured by the same method as that described in (1) above. The pH of the reaction solution was measured after the completion of the reaction. The strength of the activity was evaluated as a relative value, with the point at which maximum activity was shown taken as 100%.

Figure 2:
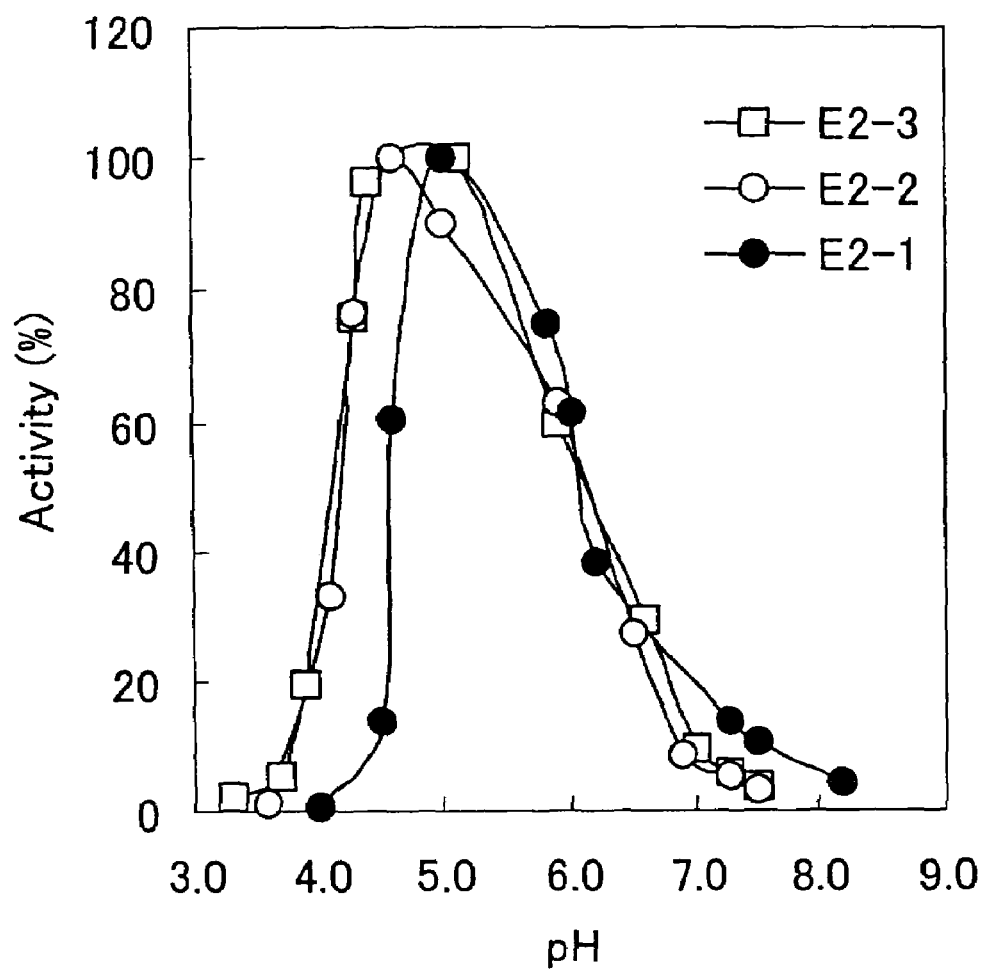
FIG. 2 shows the optimal pH of the isozymes.

As a result of these experiments, it was determined that the optimal pH values of the respective isozymes of E2 are all similar, at 4.5 to 5.0. The measurement results for the optimal pH are shown in FIG. 2.

Figure 3:
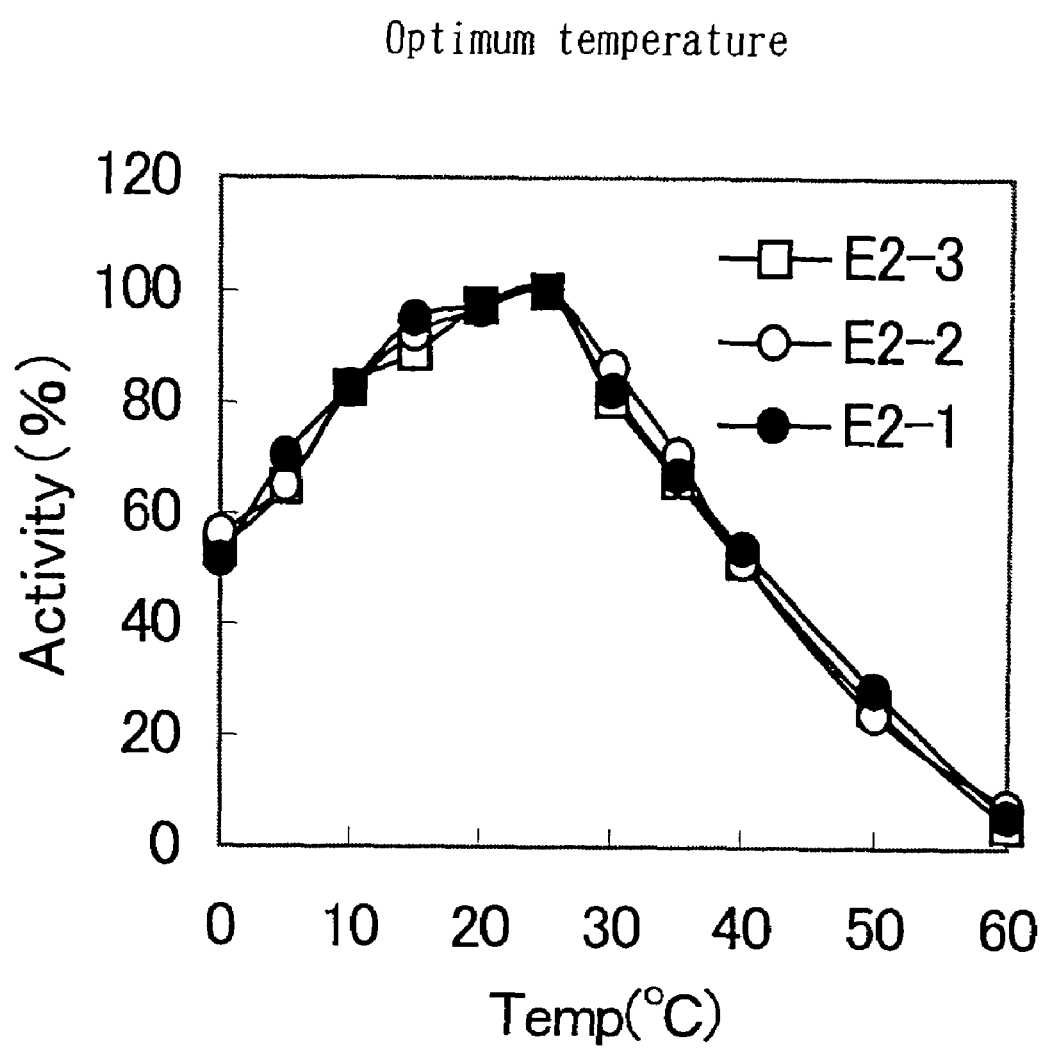
FIG. 3 shows the optimal temperature of the isozymes.

A reaction solution was prepared by the same method as that described in (1) above, and the reaction temperature was varied from 0° C. to 60° C. The strength of the activity was then evaluated as a relative value, with the point at which maximum activity was shown taken as 100%. As a result of these measurements, it was determined that the optimal temperatures of the respective isozymes of E2 are all similar, at 15° C. to 25° C. The measurement results for this optimal temperature are shown in FIG. 3.

(3) Determination of N Terminal Amino Acid Sequences of Isozymes of Lachrymatory Factor Producing Enzyme The isozymes of the abovementioned lachrymatory factor producing enzyme purified by isoelectric point electrophoresis and chromato-focusing were analyzed by the phenyl isothiocyanate method so that the N terminal amino acid sequences were determined. In this case, a G100A (HEWLETT PACKARD) was used as a protein sequencer, and a 1090 (HEWLETT PACKARD) was used as a PTH analyzer.

The N terminal amino acid sequences thus obtained were as follows:

| Sample Name | Content | Sequence | |
|---|---|---|---|
| E2-3 | large | Asp Ser Ala Asp Gly Ala Arg Lys Trp Ser | (amino acids 1 to 10 of SEQ ID NO:3) |
| E2-1-3 | small | Ser Ala Asn Gly Ala | (amino acids 2 to 6 of SEQ ID NO:3) |
| E2-2 | large | Ala Asp Gly Ala Arg | (amino acids 1 to 5 of SEQ ID NO:2) |
| E2-1 | large | Gly Ala Arg Lys Trp | (amino acids 3 to 7 of SEQ ID NO:2) |
| E2-1-2 | small | Ala Arg Lys Trp | (amino acids 4 to 7 of SEQ ID NO:2) |

(4) Synthesis of cDNA Originating in Onions

Total RNA was prepared from 2.4 g of onion bulbs by the phenol/SDS/LiCl method. Furthermore, 1.5 µg of poly A-RNA containing mRNA was isolated by oligo dT cellulose column chromatography, and cDNA was synthesized by means of an oligo dT primer and reverse transcription enzyme using this [mRNA] as a template. An mRNA Purification Kit (manufactured by Pharmacia) was used to prepare the mRNA from the total RNA, and an RTG-T-Primed First-Strand Kit (manufactured by Pharmacia) was used for the synthesis of the cDNA using the mRNA as a template.

(5) Determination of 3' Terminal Side Base Sequence of cDNA Coding for E2-1

The base sequence of the DNA was inferred from the N-terminal amino acid sequence of E2-1, and a synthetic primer 5'-GGIGCI(A/C)GIAA(A/G)TGG-3' (SEQ ID NO:10) was prepared. Furthermore, a reverse primer 5'-TG-GAGGAATTCGCGGCCGCAG-3' (SEQ ID NO:11) which was complementary to the anchor part attached to the oligo dT primer was also prepared. Using the two primers thus prepared, a PCR reaction was performed under the temperature conditions shown below by means of a Thermal Cycler (manufactured by PE Biosystems Co.) using cDNA originating in onions as a template.

Specifically, following thermal denaturation for 9 minutes at 95° C., a cycle consisting of thermal denaturation for 1 minute at 94° C., annealing for 1 minute at 43° C. and an extension reaction for 1 minute at 72° C. was repeated 40 times; afterward, an extension reaction was performed for 2 minutes at 72° C., and the reaction was stopped. As a result, a single product of approximately 660 bp was obtained.

Furthermore, in the base sequences of the primers, "/" indicates "or", and "I" indicates inosine.

(6) Analysis of 3' Terminal Side Base Sequence of cDNA Coding for E2-1 Amplified by PCR In order to determine the base sequence of approximately 660 bp that was amplified by PCR, the amplification product was cut out from an agarose gel and purified, and was then sub-cloned in a pGEM-T Easy Vector. This sub-cloned product was introduced into a *E. Coli* (XL1-Blue); then, following amplification, the plasmid was collected from the recombinant *E. Coli* and purified. Using this plasmid as a sample, the 3' terminal side base sequence was determined by the dideoxy method.

(7) Determination of 5' Terminal Side Base Sequence of cDNA coding for E2-1

The 5' RACE method was used to analyze the 5' terminal side cDNA of E2-1. In concrete terms, using the 5' RACE System Kit (LIFE TECHNOLOGIES Co.), oligo dC was tailed on the 5' terminal of cDNA synthesized from mRNA, and this was used as a template. The anchor primer 5'-GGC-CACGCGTCGACTAGTACGGGIIGGGIIGGGIIG-3' supplied with the kit, and a reverse primer 5'-TCCTCGTAC-CCTGTAAAACACTCAG-3' prepared on the basis of the sequence ascertained by analysis of the 3' terminal side cDNA of E2-1, were used as primers, and a PCR reaction was performed under the following temperature conditions using a Thermal Cycler (manufactured by PE Biosystems Co.).

Specifically, following thermal denaturation for 9 minutes at 95° C., a cycle consisting of thermal denaturation for 1 minute at 94° C., annealing for 1 minute at 55° C. and an extension reaction for 1 minute at 72° C. was repeated 40 times; afterward, an extension reaction was performed for 7 minutes at 72° C., and the reaction was stopped. As a result, a single product of approximately 430 bp was obtained.

(8) Analysis of 5' Terminal Side Base Sequence of cDNA Originating in E2-1

In order to determine the base sequence of approximately 430 bp that was amplified by PCR, the amplification product was cut out from an agarose gel and purified, and the sequence was determined by the same procedure as that used in the case of the abovementioned 3' terminal side base sequence. The full-length base sequence obtained by the analysis of the 3' side and 5' side is indicated by SEQ ID No.: 5. Furthermore, the sequence of the open reading frame part detected in the SEQ ID No.: 5 is indicated by the SEQ ID No.: 4.

(9) Amino Acid Sequence Obtained from Base Sequence

The amino acid sequence was inferred from the base sequence indicated by SEQ ID No.: 4, and when this amino acid sequence was compared with the N terminal amino acid sequence of E2-1, corresponding sequences were found; accordingly, it was confirmed that the isolated cDNA is the cDNA of the isozyme E2-1 of the lachrymatory factor producing enzyme. Furthermore, it was also confirmed that the molecular weight of E2-1 measured by MALDI-TOFMS showed good agreement with the molecular weight of the amino acid sequence obtained from the base sequence.

Molecular Weight of E2-1: Measured Value 17465, Calculated Value 17503

Furthermore, as a result of a comparative examination of the amino acid sequence of the protein that was coded for by the isolated cDNA and the amino acid sequence of the mature protein, it was found that peptides not contained in the mature protein were present on the N terminal side of the protein that was coded for by the cDNA. As a result, it was confirmed that in the case of E2-1, the mature protein is formed as a result of 16 amino acids on the N terminal side being cut following translation into the protein. This mature E2-1 amino acid sequence was indicated by SEQ ID No.: 1.

(10) Determination of Amino Acid Sequences of E2-2 and E2-3

The amino acid sequences of E2-2 and E2-3 were determined by the same method as that used in the abovementioned (2) through (9).

It was predicted from the results of an analysis of the N terminal amino acid sequences of the abovementioned isozymes that E2-2 would be a product in which the amino acids on the N terminal side are longer than those of E2-1 by two residues, and that E2-3 would be a product in which the amino acids on the N terminal side are longer than those of E2-1 by four residues. In actuality, however, when the amino acids inferred from the gene coding for E2-1 were compared with the N terminal amino acids of E2-2 and E2-3, it was ascertained that there was disagreement in only one place.

The amino acids that did not show agreement were the second aspartic acid from the N terminal in E2-2 and the fourth aspartic acid from the N terminal in E2-3. In the gene coding for E2-1, asparagine was coded. Accordingly, since it appeared that there was a possibility that the gene coding for E2-1 and the genes coding for E2-1 and E2-3 were different, the genes coding for E2-1 and E2-3 were analyzed by the same method as that used in the abovementioned case of E2-1.

First, for use in the determination of the 3' terminal side base sequence, the following three types of synthetic primers E2-3-N9-1, E2-3-N9-2 and E2-3-Asp were prepared from the sequence of nine residues of the N-terminal amino acids of E2-3.

E2-3-N9-1:
5'-
GA(C/T)AG(C/T)GCI(A/G)A(C/T)GGIGCICGIAA(A/G)TGG-3'

E2-3-N9-2:
5'-GA(C/T)TCIGCI(A/G)A(C/T)GGIGCICGIAA(A/G)TGG-3'

E2-3-Asp:
5'-GATAGTGCTGA(C/T)GGAGCTCGAAAATGG-3'

Using a combination of the E2-3-N9-1 primer with the reverse primer synthesized in (5) above, a combination of the E2-3-N9-2 primer with this reverse primer, and a combination of the E2-3-Asp primer with this reverse primer, a PCR reaction was performed by means of a Thermal Cycler (manufactured by PE Biosystems Co.), with cDNA originating in onions used as a template. Furthermore, the PCR conditions were the same as in the case of (5) above, except that the annealing temperature was changed to 53° C.

As a result of PCR, a single product of approximately 660 bp was obtained in all of the primer combinations. Furthermore, the base sequences of the three types of products obtained agreed with the sequence of E2-1 except for the primer portions. These results indicate that the 3' terminal side base sequences of the genes that code for E2-2 and E2-3 are the same as the sequence of the gene that codes for E2-1.

Next, the 5' terminal side base sequences were determined. As a result of performing sequencing twice for products amplified by the same procedure as that used in the case of (7) above, it was found that the base sequences of the amplification products all agreed with the 5' terminal side sequence of E2-1.

The above results suggest that the genes that code for E2-2 and E2-3 are the same as the gene that codes for E2-1.

Since the genes that code for the isozymes of E2 are identical, it was ascertained that the aspartic acid of the second residue from the N terminal in E2-2 and the aspartic acid of the fourth residue from the N terminal in E2-3 are translated as asparagine, and are then converted into aspartic acid afterward.

Reactions whereby asparagine is converted into aspartic acid are introduced in the Journal of Liquid Chromatography, 15 (6 & 7), 1115-1128 (1992) and the like; it is reported here that asparagine readily changes into aspartic acid when glycine is bonded to the C terminal side of asparagine.

Furthermore, the fact that the base sequences that code for E2-2 and E2-3 are identical to the cDNA sequence that codes for E2-1 was also confirmed by the fact that the molecular weight (17689) of E2-2 inferred from the base sequence more or less agreed with the measured value of the molecular weight (17722) of E2-2, and the fact that the molecular weight (17892) of E2-3 more or less agreed with the measured value of the molecular weight (17909) of E2-2.

It was demonstrated from the above results that E2-2 forms a mature protein as a result of the cutting of 14 amino acids form the N terminal side and the conversion of the asparagine constituting the second residue from the N terminal into aspartic acid following translation into a protein, and that E2-3 forms a mature protein as a result of the cutting of 12 amino acids form the N terminal side and the conversion of the asparagine constituting the fourth residue from the N terminal into aspartic acid following translation into a protein.

These results are respectively indicated by SEQ ID No.: 2 and SEQ ID No.: 3. Furthermore, the base sequence of the structure gene (ORF) consisting of 507 bases including he gene regions that code for the abovementioned E2-1, E2-2 and E2-3 is indicated by SEQ ID No.: 4, and the full-length base sequence consisting of 737 bases is indicated by SEQ ID No.: 5. Moreover, the full-length base sequence and the amino acid sequence of E2 are shown in FIG. 4.

(11) Construction of Expression Plasmids

A product (product A) of approximately 660 bp was obtained by performing a PCR reaction using the forward primer E2-3-N9-1 and a reverse primer (the reverse primer synthesized in (5) above) complementary to the anchor part attached to the oligo dT primer, and using cDNA originating in onions as a template, in accordance with the method described above in the determination of the amino acid sequences of E2-2 and E2-3 in the present example.

Furthermore, a product (product B) of approximately 660 bp was similarly obtained by performing PCR using E2-3-N9-2 as the forward primer instead of the forward primer E2-3-N9-1.

Figure 7:
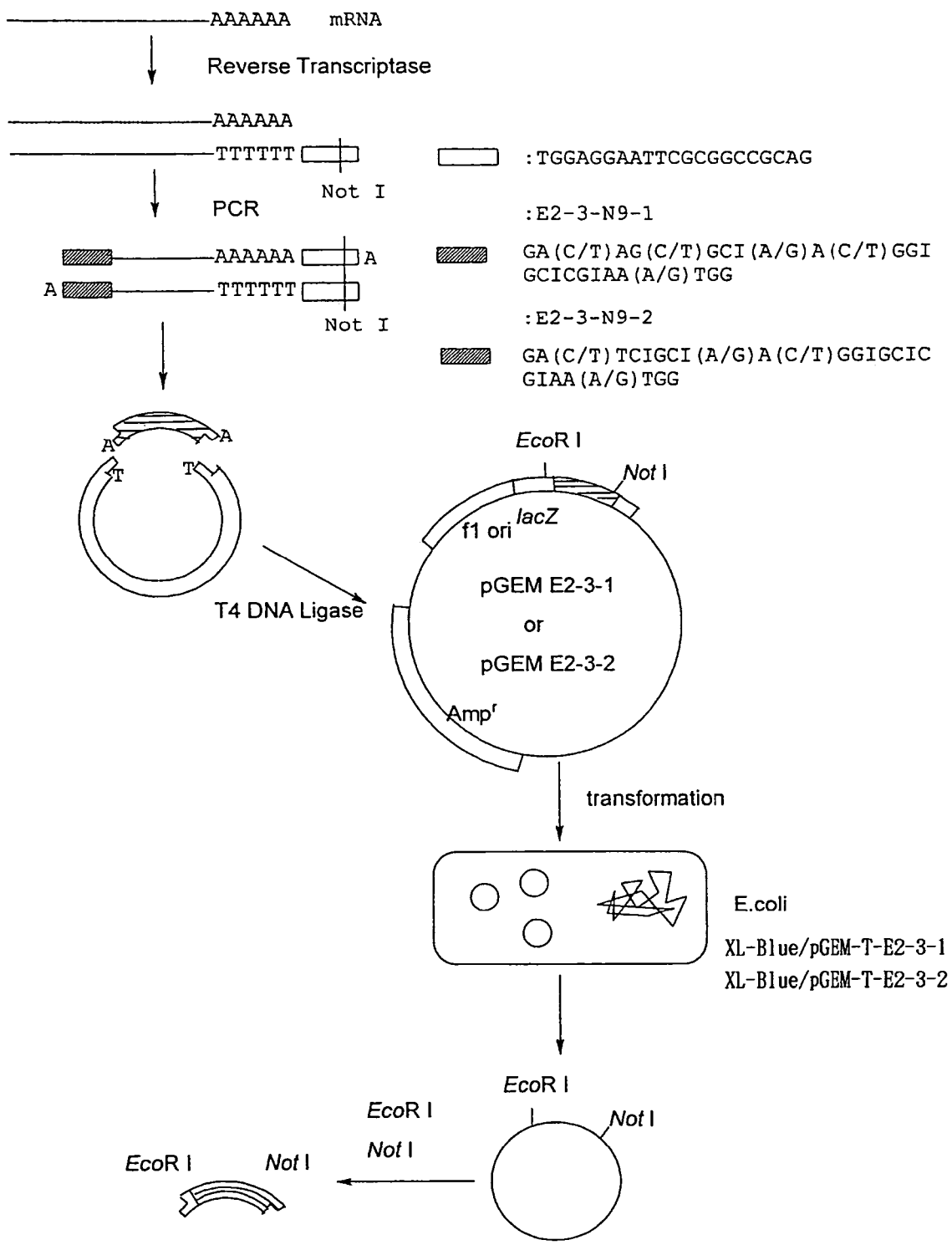
FIG. 7 shows the preparation of cDNA and sub-cloning procedure for E2-3-1 and E2-3-2.

The products A and B thus obtained were sub-cloned in a pGEM-T Easy Vector using the previously described base sequence determination method; afterward, the vectors were introduced into E. Coli (XL1-Blue), and the base sequences were analyzed. The sub-cloning procedure is shown in FIG. 7.

A E. Coli (XL1-Blue/pGEM-T-E2-3-1) with a base sequence coding for the polypeptide indicated by SEQ ID No.: 3 was obtained from the E. Coli with the pGEM-T Easy Vector into which the abovementioned product A was incorporated. The base sequence and corresponding amino acid sequence of product A introduced into XL1-Blue/pGEM-T-E2-3-1 are indicated by SEQ ID No.: 6 and SEQ ID No.: 7, and are shown in FIG. 5.

Figure 8:
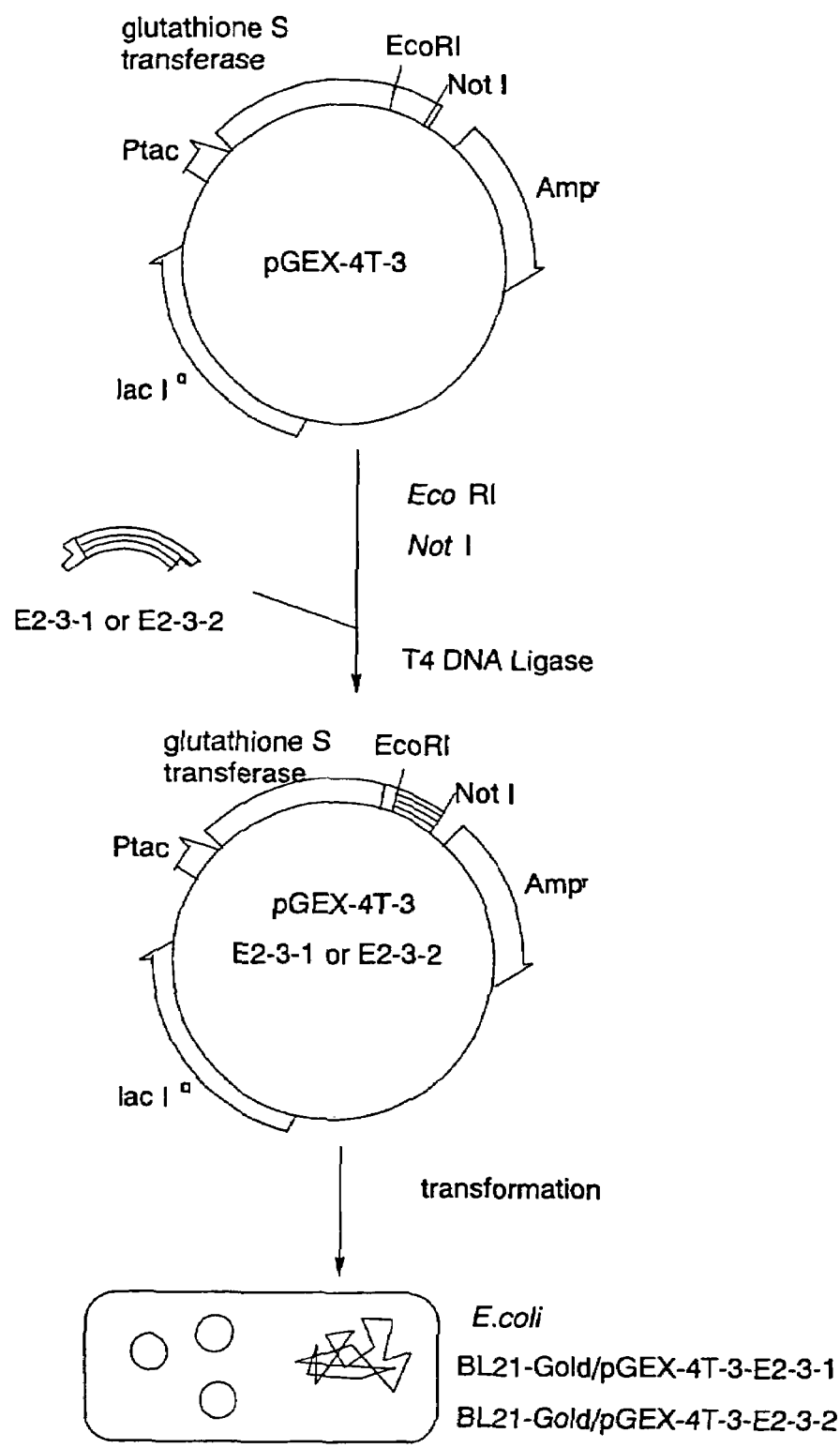
FIG. 8 shows the construction of the expression plasmid and procedure used to prepare the transformant.

Similarly, a E. Coli (XL1-Blue/pGEM-T-E2-3-2) with a base sequence coding for a polypeptide in which only the Asp in the No. 4 position of the amino acid sequence indicated by SEQ ID No.: 3 was replaced by Asn was obtained from the E. Coli with the pGEM-T Easy Vector into which the abovementioned product B was incorporated. The base sequence and corresponding amino acid sequence of product B introduced into XL1-Blue/pGEM-T-E2-3-2 are indicated by SEQ ID No.: 8 and SEQ ID No.: 9, and are shown in FIG. 6.

pGEX-4T-3 (manufactured by Amersham Pharmacia) which has a protease recognition site and multi-cloning site on the downstream side of the sequence of the glutathione S transferase (GST) gene was used as an expression vector for the protein (FIG. 8).

A large fragment obtained by cutting pGEX-4T-3 with EcoRI (manufactured by Takara Co.) and NotI (manufactured by Takara Co.), and a fragment of approximately 700 bp obtained by cutting the abovementioned pGEM-T-E2-3-1 with EcoRI and NotI, were connected, thus constructing an expression plasmid pGEX-4T-3-E2-3-1.

Similarly, a large fragment obtained by cutting pGEX-4T-3 with EcoRI and NotI and a fragment of approximately 700 bp obtained by cutting the abovementioned pGEM-T-E2-3-2 with EcoRI and NotI were connected, thus constructing an expression plasmid pGEX-4T-3-E2-3-2 as well.

(12) Preparation and Culturing of Transformant of Coliform Bacteria Using Expression Plasmids The abovementioned pGEX-4T-3-E2-3-1 was introduced into the E. Coli BL21-Gold (manufactured by STRATAGENE Co.) by the competent cell method, thus producing a transformant BL21-Gold/pGEX-4T-3-E2-3-1 (FERM BP-7675) (FIG. 8).

Similarly, furthermore, pGEX-4T-3-E2-3-2 was introduced into the E. Coli BL21-Gold (manufactured by STRATAGENE Co.), thus producing a transformant BL21-Gold/pGEX-4T-3-E2-3-2.

The transformant thus obtained were subjected to a shaken culture at 37° C. in an LB culture medium containing 100 μg/ml ampicillin. When production was induced by adding isopropyl-β-D-thiogalactopyranoside (IPTG) to the culture medium, a fused protein of GST and E2-3-1 (this fused protein is hereafter referred to as "GST-E2-3-Asp") and a fused protein of GST and E2-3-2 (this fused protein is hereafter referred to as "GST-E2-3-Asn") accumulated inside the cell mass.

(13) Isolation (Purification) of Proteins

After the transformant were cultured as described above and the cell mass was collected by centrifugal separation, the cell mass was disrupted by ultrasonic. The supernatant recovered by centrifuging was passed through a glutathione Sepharose Fast Flow column (manufactured by Amersham Pharmacia), and the GST fused proteins were adsorbed on the column. After the column was washed, the fused proteins were eluted with an eluent buffer containing reducing type glutathione, thus producing two types of purified E2-3 fused protein samples (GST-E2-3-Asp and GST-E2-3-Asn).

The two types of fused protein samples were caused to flow through a HiTrap Desalting column (manufactured by Amersham Pharmacia) so that the reducing type glutathione was removed, and the samples were again adsorbed on a glutathione Sepharose Fast Flow column. After the column was washed, the column was filled with a buffer containing thrombin, and a protease treatment was performed for 2 hours at room temperature, thus cutting the GST tags from the fused proteins. The recombinant E2-3-Asp and E2-3-Asn from which the GST tags had been removed were eluted from the column; then, Benzamidine Sepharose was added to this eluate and mixed, and the eluate was subjected to centrifugal separation so that the thrombin in the eluate was removed, thus producing two types of recombinant E2-3 samples (RC-E2-3-Asp and RC-E2-3-Asn).

(14) Lachrymatory Factor Producing Enzyme Activity of Recombinant Proteins

Lachrymatory factor producing enzyme activity was measured for a total of four samples, i. e., GST-E2-3-Asp and GST-E2-3-Asn, which were fused protein samples, and RC-E2-3-Asp and RC-E2-3-Asn, which were recombinant E2-3 samples from which the GST tags were removed.

Figure 9:
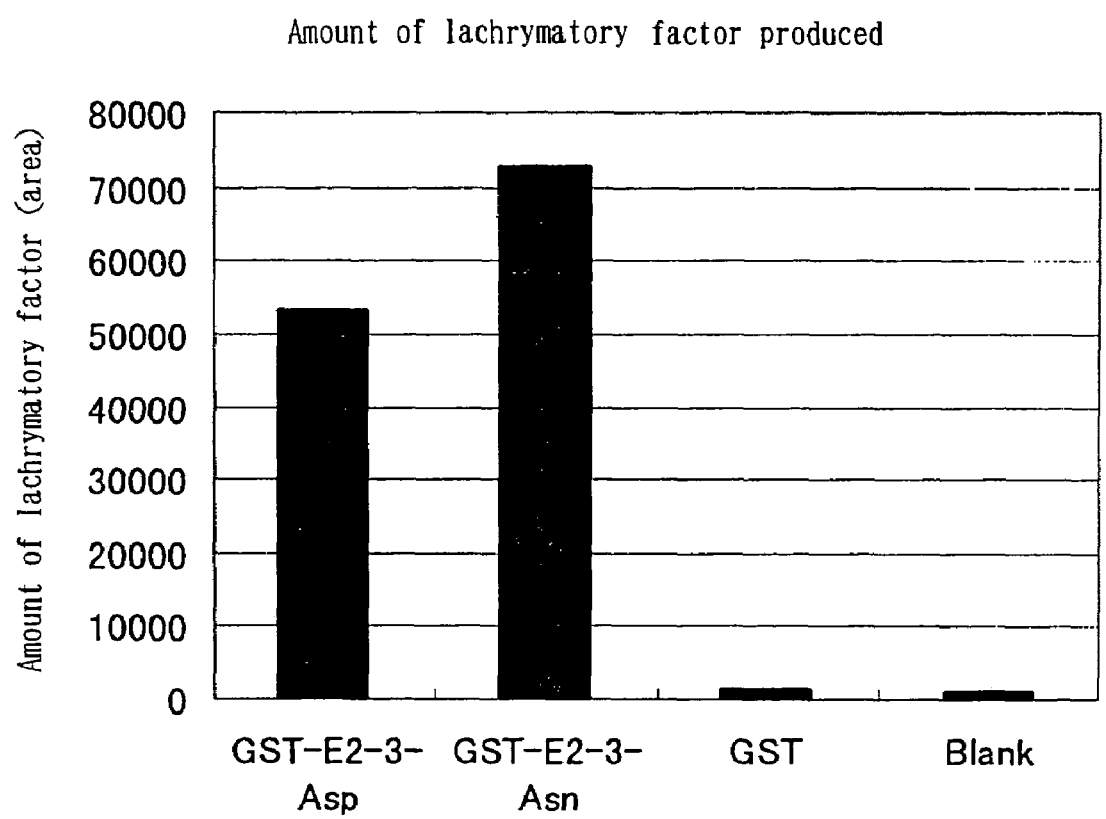
FIG. 9 shows the results of activity measurement performed in a sample in which the eluate from a glutathione Sepharose 4 Fast Flow column was diluted 5000 times.

As a result, lachrymatory factor producing enzyme activity was detected in the fused protein samples GST-E2-3-Asp and GST-E2-3-Asn. On the other hand, no lachrymatory factor producing enzyme activity was detected even when the transformant (BL21-Gold/pGEX-4T-GST) prepared with the expression plasmid pGEX-4T into which the E2-3 gene was not introduced was subjected to a glutathione Sepharose column treatment. Furthermore, a blank test performed using a phosphate buffer instead of a sample also showed no lachrymatory factor producing enzyme activity. FIG. 9 shows the results of activity measurements performed using samples that were prepared by diluting the eluate from the glutathione Sepharose Fast Flow column 5000 times.

From the above results, it was possible to confirm that lachrymatory factor producing enzyme activity is present even in the case of a fused protein n which a large protein such as GST (molecular weight: approximately 27,000) is bonded to the N terminal of E2-3.

Furthermore, since lachrymatory factor producing enzyme activity was also detected in RC-E2-3-Asp and RC-E2-3-Asn, the proteins were determined by the Bradford method, and the specific activity was calculated.

As a result, it was found that there was no difference in specific activity between RC-E2-3-Asp and RC-E2-3-Asn. Furthermore, it was found that the specific activity of E2-3 obtained by recombination with natural E2-3 was also at the same level.

| Sample Name | Specific Activity (area/mg) |
|---|---|
| RC-E2-3-Asp | $4.4 \times 10^8$ |
| RC-E2-3-Asn | $4.1 \times 10^8$ |
| Natural E2-3 | $2.5 \times 10^8$ |

INDUSTRIAL APPLICABILITY

The present invention relates to isozymes of a lachrymatory factor producing enzyme that has the activity of producing the lachrymatory factor that is generated when onions are crushed or cut, the amino acid sequences of the proteins or polypeptides of these isozymes, and the DNA that codes for these amino acid sequences. The present invention possesses the following exceptional merits: 1) Three types of isozymes of (E2-1, E2-2 and E2-3) of the E2 enzyme that have been difficult to purify in the case of conventional methods can be isolated and provided. 2) The amino acid sequences of these isozymes can be provided. 3) The base sequences that code for these isozymes can be provided. 4) The abovementioned amino acid sequences and the DNA that codes for these sequences are useful as for example markers for the selection of materials for cross breeding in the development of onion varieties in which the amount of lachrymatory factor that is produced during crushing or cutting is reduced. 5) Information obtained from the abovementioned DNA is useful in the design of antisense nucleotides that are needed in order to inhibit the amount of expression of the abovementioned enzyme. 6) The abovementioned lachrymatory factor producing enzyme can be efficiently created by genetic recombination techniques. 7) The efficient production of lachrymatory factor, which is useful for treating alacrima (dry eye) and the like, can be realized.

REFERENCE TO DEPOSITED MICROORGANISMS

Name and Address of Depositary Authority: Dokuritsu Gyosei Hojin Sangyo Gijutsu Sogo Kenkyujo [National Institute of Advanced Industrial Science and Technology], International Patent Organism Depositary (Address: AIST Tsukuba Central 6, 1-1, Higashi 1-chome, Tsukuba-shi, Ibaraki-ken, 305-8566 Japan)

Date of Original Deposit: Jul. 25, 2001

Accession No.: FERM BP-7675

Identification of Microorganism: E2-3-1

The invention claimed is:

1. An isolated isozyme of a lachrymatory factor producing enzyme from onions, which converts lachrymatory factor precursors to lachrymatory factor and which comprises an N-terminal amino acid sequence selected from the group consisting of amino acids 1 to 5 of SEQ ID NO:1, amino acids 1 to 5 of SEQ ID NO:2, and amino acids 1 to 5 of SEQ ID NO:3.

2. An isolated isozyme of lachrymatory factor producing enzyme, which consists of SEQ ID NO:1.

3. An isolated isozyme of lachrymatory factor producing enzyme, which consists of SEQ ID NO:2.

4. An isolated isozyme of lachrymatory factor producing enzyme, which consists of SEQ ID NO:3.

* * * * *

SEQUENCE LISTING

<160> NUMBER OF SEQ ID NOS: 9

<210> SEQ ID NO 1
<211> LENGTH: 153
<212> TYPE: PRT
<213> ORGANISM: Allium cepa

<400> SEQUENCE: 1

Gly Ala Arg Lys Trp Ser Gly Lys Val His Ala Leu Leu Pro Asn Thr
1               5                   10                  15

Lys Pro Glu Gln Ala Trp Thr Leu Leu Lys Asp Phe Ile Asn Leu His
            20                  25                  30

Lys Val Met Pro Ser Leu Ser Val Cys Glu Leu Val Glu Gly Glu Ala

```
                35                  40                  45
Asn Val Val Gly Cys Val Arg Tyr Val Lys Gly Ile Met His Pro Ile
         50                  55                  60
Glu Glu Glu Phe Trp Ala Lys Glu Lys Leu Val Ala Leu Asp Asn Lys
 65                  70                  75                  80
Asn Met Ser Tyr Ser Tyr Ile Phe Thr Glu Cys Phe Thr Gly Tyr Glu
                 85                  90                  95
Asp Tyr Thr Ala Thr Met Gln Ile Val Glu Gly Pro Glu His Lys Gly
            100                 105                 110
Ser Arg Phe Asp Trp Ser Phe Gln Cys Lys Tyr Ile Glu Gly Met Thr
        115                 120                 125
Glu Ser Ala Phe Thr Glu Ile Leu Gln His Trp Ala Thr Glu Ile Gly
    130                 135                 140
Gln Lys Ile Glu Glu Val Cys Ser Ala
145                 150
```

```
<210> SEQ ID NO 2
<211> LENGTH: 155
<212> TYPE: PRT
<213> ORGANISM: Allium cepa

<400> SEQUENCE: 2

Ala Asp Gly Ala Arg Lys Trp Ser Gly Lys Val His Ala Leu Leu Pro
  1               5                  10                  15
Asn Thr Lys Pro Glu Gln Ala Trp Thr Leu Leu Lys Asp Phe Ile Asn
             20                  25                  30
Leu His Lys Val Met Pro Ser Leu Ser Val Cys Glu Leu Val Glu Gly
         35                  40                  45
Glu Ala Asn Val Val Gly Cys Val Arg Tyr Val Lys Gly Ile Met His
     50                  55                  60
Pro Ile Glu Glu Glu Phe Trp Ala Lys Glu Lys Leu Val Ala Leu Asp
 65                  70                  75                  80
Asn Lys Asn Met Ser Tyr Ser Tyr Ile Phe Thr Glu Cys Phe Thr Gly
                 85                  90                  95
Tyr Glu Asp Tyr Thr Ala Thr Met Gln Ile Val Glu Gly Pro Glu His
            100                 105                 110
Lys Gly Ser Arg Phe Asp Trp Ser Phe Gln Cys Lys Tyr Ile Glu Gly
        115                 120                 125
Met Thr Glu Ser Ala Phe Thr Glu Ile Leu Gln His Trp Ala Thr Glu
    130                 135                 140
Ile Gly Gln Lys Ile Glu Glu Val Cys Ser Ala
145                 150                 155
```

```
<210> SEQ ID NO 3
<211> LENGTH: 157
<212> TYPE: PRT
<213> ORGANISM: Allium cepa

<400> SEQUENCE: 3

Asp Ser Ala Asp Gly Ala Arg Lys Trp Ser Gly Lys Val His Ala Leu
  1               5                  10                  15
Leu Pro Asn Thr Lys Pro Glu Gln Ala Trp Thr Leu Leu Lys Asp Phe
             20                  25                  30
Ile Asn Leu His Lys Val Met Pro Ser Leu Ser Val Cys Glu Leu Val
         35                  40                  45
Glu Gly Glu Ala Asn Val Val Gly Cys Val Arg Tyr Val Lys Gly Ile
```

```
                50                       55                      60
Met His Pro Ile Glu Glu Glu Phe Trp Ala Lys Glu Lys Leu Val Ala
 65                      70                      75                      80

Leu Asp Asn Lys Asn Met Ser Tyr Ser Tyr Ile Phe Thr Glu Cys Phe
                         85                      90                      95

Thr Gly Tyr Glu Asp Tyr Thr Ala Thr Met Gln Ile Val Glu Gly Pro
                        100                     105                     110

Glu His Lys Gly Ser Arg Phe Asp Trp Ser Phe Gln Cys Lys Tyr Ile
                115                     120                     125

Glu Gly Met Thr Glu Ser Ala Phe Thr Glu Ile Leu Gln His Trp Ala
        130                     135                     140

Thr Glu Ile Gly Gln Lys Ile Glu Glu Val Cys Ser Ala
145                     150                     155

<210> SEQ ID NO 4
<211> LENGTH: 737
<212> TYPE: DNA
<213> ORGANISM: Allium cepa

<400> SEQUENCE: 4
acaattcaga ctcacattac gttatatcaa aagagattgtc caatcagaaa aaatggagct    60
aaatcctggt gcacctgctg tagtcgctga tagtgctaac ggagctcgaa atggagcgg    120 caaagtccat gctttgcttc caaatacaaa gccagagcaa gcatggacac tactaaaaga   180
ctttattaac cttcacaagg tcatgccttc gttgtcagtc tgtgaactgg tagaaggtga   240
ggccaatgtt gttggttgtg ttcgctacgt taaaggtata atgcacccaa tagaaggga    300 attttgggcc aaggagaagc tggtggcgct ggataataag aacatgagct acagttatat   360
ttttactgag tgttttacag ggtacgagga ttacacggct accatgcaaa tagtggaggg   420
tcctgagcac aagggaagta gatttgactg gtcttttcag tgcaagtata tcgagggtat   480
gactgaatct gcattcaccg agattctgca gcattgggct actgagatag gtcagaaaat   540
cgaagaggtt tgcagtgctt gatcatgaat atcggttttc agtgctgtga tgcattatgt   600 gtctttttaaa ccttgtcttg tgatataata aagtaacgta atatgtgcat gtaataagta   660
agactgagtg ttgtgtgttc aataaaaaag aatttgcttt ttgcaagttc tagtgctttt   720
caaaaaaaaa aaaaaaa                                                   737

<210> SEQ ID NO 5
<211> LENGTH: 507
<212> TYPE: DNA
<213> ORGANISM: Allium cepa

<400> SEQUENCE: 5
atggagctaa atcctggtgc acctgctgta gtcgctgata gtgctaacgg agctcgaaaa    60
tggagcggca aagtccatgc tttgcttcca aatacaaagc cagagcaagc atggacacta   120
ctaaaagact tattaacct tcacaaggtc atgccttcgt tgtcagtctg tgaactggta   180
gaaggtgagg ccaatgttgt tggttgtgtt cgctacgtta aaggtataat gcacccaata   240
gaagaggaat ttgggccaa ggagaagctg gtggcgctgg ataataagaa catgagctac   300
agttatattt ttactgagtg ttttacaggg tacgaggatt acacggctac catgcaaata   360
gtggagggtc ctgagcacaa gggaagtaga tttgactggt cttttcagtg caagtatatc   420
gagggtatga ctgaatctgc attcaccgag attctgcagc attgggctac tgagataggt   480
cagaaaatcg aagaggtttg cagtgct                                       507
```

<210> SEQ ID NO 6
<211> LENGTH: 673
<212> TYPE: DNA
<213> ORGANISM: Allium cepa

<400> SEQUENCE: 6

```
aattcgattg atagtgcgga cggggcgcgg aaatggagcg gcaaagtcca tgctttgctt      60
ccaaatacaa agccggagca agcatggaca ctactaaaag actttattaa ccttcacaag     120
gtcatgcctt cgttgtcagt ctgtgaactg gtagaaggtg aggccaatgt tgttggttgt     180
gttcgctacg ttaaaggtat aatgcaccca atagaagagg aatttggggc caaggagaag     240
ctggtggcgc tggataataa gaacatgagc tacagttata ttttactga gtgttttaca      300
gggtacgagg attacacggc taccatgcaa atagtggagg tcctgagca aagggaagt      360
agatttgact ggtcttttca gtgcaagtat atcgagggta tgactgaatc tgcattcacc     420
gagattctgc agcattgggc tactgagata ggtcagaaaa tcgaagaggt ttgcagtgct     480
tgatcatgaa atcgtttat gctgtgatgc attatttgtg ttttaaaccg tgtcctgtga      540
tataataaag taacgtcatt tgtgcacgta ataagtaaag cccgagtgtt gtgtgttcaa     600
taaaaagaa cttgctttt gcaggttcta gtgctttca aaaaaaaaa aaaaaaaaa         660
aaaaaattcc tgc                                                        673
```

<210> SEQ ID NO 7
<211> LENGTH: 160
<212> TYPE: PRT
<213> ORGANISM: Allium cepa

<400> SEQUENCE: 7

```
Asn Ser Ile Asp Ser Ala Asp Gly Ala Arg Lys Trp Ser Gly Lys Val
1               5                   10                  15
His Ala Leu Leu Pro Asn Thr Lys Pro Glu Gln Ala Trp Thr Leu Leu
            20                  25                  30
Lys Asp Phe Ile Asn Leu His Lys Val Met Pro Ser Leu Ser Val Cys
        35                  40                  45
Glu Leu Val Glu Gly Glu Ala Asn Val Val Gly Cys Val Arg Tyr Val
    50                  55                  60
Lys Gly Ile Met His Pro Ile Glu Glu Glu Phe Trp Ala Lys Glu Lys
65                  70                  75                  80
Leu Val Ala Leu Asp Asn Lys Asn Met Ser Tyr Ser Tyr Ile Phe Thr
                85                  90                  95
Glu Cys Phe Thr Gly Tyr Glu Asp Tyr Thr Ala Thr Met Gln Ile Val
            100                 105                 110
Glu Gly Pro Glu His Lys Gly Ser Arg Phe Asp Trp Ser Phe Gln Cys
        115                 120                 125
Lys Tyr Ile Glu Gly Met Thr Glu Ser Ala Phe Thr Glu Ile Leu Gln
    130                 135                 140
His Trp Ala Thr Glu Ile Gly Gln Lys Ile Glu Glu Val Cys Ser Ala
145                 150                 155                 160
```

<210> SEQ ID NO 8
<211> LENGTH: 673
<212> TYPE: DNA
<213> ORGANISM: Allium cepa

<400> SEQUENCE: 8

-continued

```
aattcgattg attcggcgaa tggggcgcgg aagtggagcg gcaaagtcca tgctttgctt      60
ccaaatacaa agccagagca agcatggaca ctactaaaag actttattaa ccttcacaag     120
gtcatgcctt cgttgtcagt ctgtgaactg gtagaaggtg aggccaatgt tgttggttgt     180
gttcgctacg ttaaaggtat aatgcaccca atagaagagg aattttgggc caaggagaag     240
ctggtggcgc tggataataa gaacatgagc tacagttata ttttactga gtgttttaca     300 gggtacgagg attacacggc taccatgcaa atagtggagg tcctgagca aagggaagt      360 agatttgact ggtctttca gtgcaagtat atcgagggta tgactgaatc tgcattcacc     420
gagattctgc agcattgggc tactgagata ggtcagaaaa tcgaagaggt ttgcagtgct     480
tgatcatgaa atcggtttt cagtgctgtg atgcattatg tgtcttttaa accttgtctt     540
gtgatataat aaagtaacgt aatatgtgca tgtaataagt aagactgagt gttgtgtgtt     600
caataaaaaa gaatttgctt tttgcaagtt ctagtgcttt tcaaaaaaaa aaaaaaaaa     660 aaaaaattcc tgc                                                        673
```

```
<210> SEQ ID NO 9
<211> LENGTH: 160
<212> TYPE: PRT
<213> ORGANISM: Allium cepa

<400> SEQUENCE: 9

Asn Ser Ile Asp Ser Ala Asn Gly Ala Arg Lys Trp Ser Gly Lys Val
1               5                   10                  15

His Ala Leu Leu Pro Asn Thr Lys Pro Glu Gln Ala Trp Thr Leu Leu
            20                  25                  30

Lys Asp Phe Ile Asn Leu His Lys Val Met Pro Ser Leu Ser Val Cys
        35                  40                  45

Glu Leu Val Glu Gly Glu Ala Asn Val Val Gly Cys Val Arg Tyr Val
    50                  55                  60

Lys Gly Ile Met His Pro Ile Glu Glu Phe Trp Ala Lys Glu Lys
65                  70                  75                  80

Leu Val Ala Leu Asp Asn Lys Asn Met Ser Tyr Ser Tyr Ile Phe Thr
                85                  90                  95

Glu Cys Phe Thr Gly Tyr Glu Asp Tyr Thr Ala Thr Met Gln Ile Val
            100                 105                 110

Glu Gly Pro Glu His Lys Gly Ser Arg Phe Asp Trp Ser Phe Gln Cys
        115                 120                 125

Lys Tyr Ile Glu Gly Met Thr Glu Ser Ala Phe Thr Glu Ile Leu Gln
    130                 135                 140

His Trp Ala Thr Glu Ile Gly Gln Lys Ile Glu Glu Val Cys Ser Ala
145                 150                 155                 160
```